United States Patent
Patterson et al.

(10) Patent No.: US 9,615,935 B2
(45) Date of Patent: Apr. 11, 2017

(54) THERMALLY ACTIVATED SHAPE MEMORY SPRING ASSEMBLIES FOR IMPLANT EXPANSION

(71) Applicant: Titan Spine, LLC, Mequon, WI (US)

(72) Inventors: Chad J. Patterson, Port Washington, WI (US); Eric M. Gardner, Port Washington, WI (US)

(73) Assignee: Titan Spine, LLC, Mequon, WI (US)

( * ) Notice: Subject to any disclaimer, the term of this patent is extended or adjusted under 35 U.S.C. 154(b) by 438 days.

(21) Appl. No.: 14/168,152

(22) Filed: Jan. 30, 2014

(65) Prior Publication Data
US 2015/0209152 A1    Jul. 30, 2015

(51) Int. Cl.
*A61F 2/44*     (2006.01)
*A61F 2/30*     (2006.01)

(52) U.S. Cl.
CPC .............. *A61F 2/4455* (2013.01); *A61F 2/44* (2013.01); *A61F 2002/30092* (2013.01); *A61F 2002/30093* (2013.01); *A61F 2002/30476* (2013.01); *A61F 2002/30556* (2013.01); *A61F 2002/30565* (2013.01); *A61F 2002/30579* (2013.01)

(58) Field of Classification Search
CPC .. A61F 2002/30093; A61F 2002/30565; A61F 2/44
USPC ............................................ 623/17.11–17.16
See application file for complete search history.

(56) References Cited

U.S. PATENT DOCUMENTS

| 4,309,777 A * | 1/1982 | Patil ....................... A61F 2/442 606/247 |
| 4,314,876 A | 2/1982 | Kremer et al. |
| 4,834,757 A | 5/1989 | Brantigan |
| 4,904,261 A | 2/1990 | Dove et al. |
| 5,015,247 A | 5/1991 | Michelson |
| 5,071,437 A | 12/1991 | Steffee |
| 5,258,098 A | 11/1993 | Wagner et al. |
| 5,306,308 A | 4/1994 | Gross et al. |
| 5,306,309 A | 4/1994 | Wagner et al. |

(Continued)

FOREIGN PATENT DOCUMENTS

| EP | 0599419 | 6/1994 |
| EP | 0916323 | 5/1999 |

(Continued)

OTHER PUBLICATIONS

European Search Report issued in related application EP 15 15 3073.

(Continued)

*Primary Examiner* — David Bates
(74) *Attorney, Agent, or Firm* — Stradley Ronon Stevens & Young, LLP

(57) ABSTRACT

Thermal memory springs may form arches, or have coils or spring arms and truss arms that expand from a relaxed state when the thermal memory springs warm to a temperature that is about the body temperature of a human being. The thermal memory springs may be used to expand interbody implants from a compact state into an expanded state once the implant has been inserted into the desired location within the body and the thermal memory springs that form a part of the implant warms to body temperature. Ends of the expanded thermal memory spring may contact a bone surface, thereby being an anti-expulsion edge.

12 Claims, 20 Drawing Sheets

(56) References Cited

U.S. PATENT DOCUMENTS

| | | | |
|---|---|---|---|
| 5,425,772 A | 6/1995 | Brantigan | |
| 5,443,514 A | 8/1995 | Steffee | |
| 5,456,723 A | 10/1995 | Steinemann et al. | |
| 5,507,815 A | 4/1996 | Wagner et al. | |
| 5,571,188 A | 11/1996 | Ellingsen et al. | |
| 5,603,338 A | 2/1997 | Beaty | |
| 5,609,635 A | 3/1997 | Michelson | |
| 5,702,449 A | 12/1997 | McKay | |
| 5,749,916 A * | 5/1998 | Richelsoph | A61F 2/4455 606/247 |
| 5,755,798 A | 5/1998 | Papavero et al. | |
| 5,766,252 A | 6/1998 | Henry et al. | |
| 5,776,199 A | 7/1998 | Michelson | |
| 5,827,328 A * | 10/1998 | Buttermann | A61F 2/442 623/17.13 |
| 5,860,973 A | 1/1999 | Michelson | |
| 5,863,201 A | 1/1999 | Lazzara et al. | |
| 5,865,845 A | 2/1999 | Thalgott | |
| 5,876,453 A | 3/1999 | Beaty | |
| 5,885,079 A | 3/1999 | Niznick | |
| 5,888,224 A | 3/1999 | Beckers et al. | |
| 5,922,029 A | 7/1999 | Wagner et al. | |
| 5,968,098 A | 10/1999 | Winslow | |
| 5,984,922 A | 11/1999 | McKay | |
| 6,033,582 A | 3/2000 | Lee et al. | |
| 6,039,762 A | 3/2000 | McKay | |
| 6,059,829 A | 5/2000 | Schlapfer et al. | |
| 6,080,158 A | 6/2000 | Lin | |
| 6,086,613 A | 7/2000 | Camino et al. | |
| 6,096,107 A | 8/2000 | Caracostas et al. | |
| 6,123,705 A | 9/2000 | Michelson | |
| 6,136,031 A * | 10/2000 | Middleton | A61F 2/30744 623/17.16 |
| 6,143,032 A | 11/2000 | Schafer et al. | |
| 6,176,882 B1 | 1/2001 | Biedermann et al. | |
| 6,183,255 B1 | 2/2001 | Oshida | |
| 6,193,757 B1 | 2/2001 | Foley et al. | |
| 6,193,762 B1 | 2/2001 | Wagner et al. | |
| 6,241,770 B1 | 6/2001 | Michelson | |
| 6,241,771 B1 | 6/2001 | Gresser et al. | |
| 6,245,108 B1 | 6/2001 | Biscup | |
| 6,296,664 B1 | 10/2001 | Middleton | |
| 6,302,914 B1 | 10/2001 | Michelson | |
| 6,342,074 B1 | 1/2002 | Simpson | |
| 6,344,057 B1 | 2/2002 | Rabbe et al. | |
| 6,350,283 B1 | 2/2002 | Michelson | |
| 6,375,681 B1 | 4/2002 | Truscott | |
| 6,387,130 B1 | 5/2002 | Stone et al. | |
| 6,395,031 B1 | 5/2002 | Foley et al. | |
| 6,423,095 B1 | 7/2002 | Van Hoeck et al. | |
| 6,425,920 B1 | 7/2002 | Hamada | |
| 6,432,140 B1 | 8/2002 | Lin | |
| 6,436,102 B1 | 8/2002 | Ralph et al. | |
| 6,440,169 B1 * | 8/2002 | Elberg | A61B 17/7062 623/17.11 |
| 6,447,544 B1 | 9/2002 | Michelson | |
| 6,458,159 B1 | 10/2002 | Thalgott | |
| 6,478,823 B1 | 11/2002 | Michelson | |
| 6,482,233 B1 | 11/2002 | Aebi et al. | |
| 6,485,517 B1 | 11/2002 | Michelson | |
| 6,491,723 B1 | 12/2002 | Beaty | |
| 6,520,993 B2 | 2/2003 | James et al. | |
| 6,520,996 B1 * | 2/2003 | Manasas | B22F 3/1055 623/17.14 |
| 6,558,424 B2 | 5/2003 | Thalgott | |
| 6,569,201 B2 | 5/2003 | Moumene et al. | |
| 6,579,318 B2 | 6/2003 | Varga et al. | |
| 6,592,624 B1 | 7/2003 | Fraser et al. | |
| 6,599,322 B1 | 7/2003 | Amrich et al. | |
| 6,610,089 B1 | 8/2003 | Liu et al. | |
| 6,620,332 B2 | 9/2003 | Amrich | |
| 6,635,086 B2 | 10/2003 | Lin | |
| 6,652,765 B1 | 11/2003 | Beaty | |
| 6,676,703 B2 | 1/2004 | Biscup | |
| 6,702,855 B1 | 3/2004 | Steinemann et al. | |
| 6,719,794 B2 | 4/2004 | Gerber et al. | |
| 6,726,720 B2 | 4/2004 | Ross et al. | |
| 6,730,127 B2 | 5/2004 | Michelson | |
| 6,740,118 B2 | 5/2004 | Eisermann et al. | |
| 6,743,231 B1 | 6/2004 | Gray et al. | |
| 6,758,849 B1 | 7/2004 | Michelson | |
| 6,833,006 B2 | 12/2004 | Foley et al. | |
| 6,890,355 B2 | 5/2005 | Michelson | |
| 6,902,581 B2 | 6/2005 | Walkenhorst et al. | |
| 6,911,249 B2 | 6/2005 | Wagner et al. | |
| 6,923,810 B1 | 8/2005 | Michelson | |
| 6,964,687 B1 | 11/2005 | Bernard et al. | |
| 6,974,480 B2 | 12/2005 | Messerli et al. | |
| 6,981,975 B2 | 1/2006 | Michelson | |
| 7,018,412 B2 | 3/2006 | Ferreira et al. | |
| 7,018,418 B2 | 3/2006 | Amrich et al. | |
| 7,041,137 B2 | 5/2006 | Fulton et al. | |
| 7,044,972 B2 | 5/2006 | Mathys, Jr. et al. | |
| 7,048,870 B1 | 5/2006 | Ellingsen et al. | |
| 7,060,073 B2 | 6/2006 | Frey et al. | |
| 7,066,961 B2 | 6/2006 | Michelson | |
| 7,077,864 B2 | 7/2006 | Byrd, III et al. | |
| 7,087,085 B2 | 8/2006 | Steinemann et al. | |
| 7,112,224 B2 | 9/2006 | Liu et al. | |
| 7,128,760 B2 | 10/2006 | Michelson | |
| 7,137,997 B2 | 11/2006 | Paul | |
| 7,141,068 B2 | 11/2006 | Ross et al. | |
| 7,144,428 B2 | 12/2006 | Anitua | |
| 7,166,129 B2 | 1/2007 | Michelson | |
| 7,169,183 B2 | 1/2007 | Liu et al. | |
| D539,934 S | 4/2007 | Blain | |
| 7,201,775 B2 | 4/2007 | Gorensek et al. | |
| D541,940 S | 5/2007 | Blain | |
| 7,220,280 B2 | 5/2007 | Kast et al. | |
| 7,223,289 B2 | 5/2007 | Trieu et al. | |
| 7,226,480 B2 | 6/2007 | Thalgott | |
| 7,238,186 B2 | 7/2007 | Zdeblick et al. | |
| 7,238,203 B2 | 7/2007 | Bagga et al. | |
| 7,244,275 B2 | 7/2007 | Michelson | |
| 7,250,060 B2 | 7/2007 | Trieu | |
| 7,255,698 B2 | 8/2007 | Michelson | |
| 7,288,093 B2 | 10/2007 | Michelson | |
| 7,311,734 B2 | 12/2007 | Van Hoeck et al. | |
| D564,095 S | 3/2008 | Blain | |
| 7,347,873 B2 | 3/2008 | Paul et al. | |
| D566,276 S | 4/2008 | Blain | |
| 7,368,065 B2 | 5/2008 | Yang et al. | |
| 7,410,501 B2 | 8/2008 | Michelson | |
| 7,501,073 B2 | 3/2009 | Wen et al. | |
| 7,503,933 B2 | 3/2009 | Michelson | |
| 7,517,363 B2 | 4/2009 | Rogers et al. | |
| D599,019 S | 8/2009 | Pimenta et al. | |
| 7,569,074 B2 | 8/2009 | Eisermann et al. | |
| 7,608,107 B2 | 10/2009 | Michelson | |
| 7,615,078 B2 | 11/2009 | White et al. | |
| 7,621,950 B1 * | 11/2009 | Globerman | C25F 3/22 411/34 |
| 7,655,042 B2 | 2/2010 | Foley et al. | |
| 7,662,186 B2 | 2/2010 | Bagga et al. | |
| 7,662,190 B2 | 2/2010 | Steinemann et al. | |
| 7,744,612 B2 | 6/2010 | Blain | |
| 7,846,183 B2 | 12/2010 | Blain | |
| 7,901,462 B2 | 3/2011 | Yang et al. | |
| 7,998,172 B2 | 8/2011 | Blain | |
| 8,057,546 B2 * | 11/2011 | Studer | A61F 2/4425 623/17.11 |
| 8,062,304 B2 | 11/2011 | Blain et al. | |
| 8,100,955 B2 | 1/2012 | Blain et al. | |
| 8,142,355 B2 | 3/2012 | Blain et al. | |
| 8,172,854 B2 | 5/2012 | Blain et al. | |
| 8,262,737 B2 | 9/2012 | Bagga et al. | |
| 8,308,801 B2 * | 11/2012 | Halverson | A61F 2/4425 623/17.13 |
| 8,328,818 B1 * | 12/2012 | Seifert | A61B 17/66 606/105 |
| 8,529,626 B2 * | 9/2013 | Seme | A61B 17/7062 606/249 |

(56) References Cited

U.S. PATENT DOCUMENTS

| | | | |
|---|---|---|---|
| 8,685,096 B2 * | 4/2014 | Davenport | A61F 2/442 623/17.11 |
| 8,808,385 B1 * | 8/2014 | Smith | A61F 2/4455 623/17.11 |
| 2001/0014826 A1 | 8/2001 | Biedermann et al. | |
| 2001/0016777 A1 | 8/2001 | Biscup | |
| 2001/0039454 A1 | 11/2001 | Ricci et al. | |
| 2001/0047208 A1 | 11/2001 | Michelson | |
| 2002/0049497 A1 | 4/2002 | Mason | |
| 2002/0087212 A1 | 7/2002 | James et al. | |
| 2002/0099443 A1 | 7/2002 | Messerli et al. | |
| 2002/0128713 A1 * | 9/2002 | Ferree | A61F 2/30742 623/17.11 |
| 2002/0128716 A1 | 9/2002 | Cohen et al. | |
| 2002/0138142 A1 | 9/2002 | Castro et al. | |
| 2002/0156529 A1 | 10/2002 | Li et al. | |
| 2002/0161443 A1 | 10/2002 | Michelson | |
| 2002/0173854 A1 | 11/2002 | Amrich | |
| 2002/0188294 A1 | 12/2002 | Couture et al. | |
| 2003/0009223 A1 * | 1/2003 | Fehling | A61F 2/30742 623/17.13 |
| 2003/0014116 A1 | 1/2003 | Ralph et al. | |
| 2003/0083668 A1 | 5/2003 | Rogers et al. | |
| 2003/0105527 A1 | 6/2003 | Bresina | |
| 2003/0109928 A1 | 6/2003 | Pasquet et al. | |
| 2003/0153975 A1 | 8/2003 | Byrd, III et al. | |
| 2003/0176925 A1 | 9/2003 | Paponneau | |
| 2003/0181980 A1 | 9/2003 | Berry et al. | |
| 2003/0181981 A1 | 9/2003 | Lemaire | |
| 2003/0187506 A1 | 10/2003 | Ross et al. | |
| 2003/0191531 A1 | 10/2003 | Berry et al. | |
| 2004/0073314 A1 | 4/2004 | White et al. | |
| 2004/0117019 A1 | 6/2004 | Trieu et al. | |
| 2004/0117020 A1 | 6/2004 | Frey et al. | |
| 2004/0122518 A1 | 6/2004 | Rhoda | |
| 2004/0127993 A1 | 7/2004 | Kast et al. | |
| 2004/0134886 A1 | 7/2004 | Wagner et al. | |
| 2004/0153154 A1 | 8/2004 | Dinkelacker | |
| 2004/0153160 A1 | 8/2004 | Carrasco | |
| 2004/0162616 A1 | 8/2004 | Simonton et al. | |
| 2004/0167632 A1 | 8/2004 | Wen et al. | |
| 2004/0210309 A1 | 10/2004 | Denzer et al. | |
| 2004/0230306 A1 | 11/2004 | Hoeck et al. | |
| 2004/0265780 A1 | 12/2004 | Robb et al. | |
| 2004/0267367 A1 | 12/2004 | O'Neil | |
| 2005/0021150 A1 | 1/2005 | Michelson | |
| 2005/0027360 A1 | 2/2005 | Webb et al. | |
| 2005/0038512 A1 | 2/2005 | Michelson | |
| 2005/0043796 A1 * | 2/2005 | Grant | A61F 2/442 623/17.11 |
| 2005/0060034 A1 | 3/2005 | Berry et al. | |
| 2005/0075734 A1 | 4/2005 | Fulton et al. | |
| 2005/0085913 A1 | 4/2005 | Fraser et al. | |
| 2005/0119758 A1 | 6/2005 | Alexander et al. | |
| 2005/0131416 A1 | 6/2005 | Jansen et al. | |
| 2005/0147942 A1 | 7/2005 | Hall | |
| 2005/0159814 A1 | 7/2005 | Karahalios | |
| 2005/0161120 A1 | 7/2005 | Inagaki et al. | |
| 2005/0165483 A1 | 7/2005 | Ray et al. | |
| 2005/0203630 A1 | 9/2005 | Pope et al. | |
| 2005/0209698 A1 | 9/2005 | Gordon et al. | |
| 2005/0234557 A1 * | 10/2005 | Lambrecht | A61B 5/1076 623/17.16 |
| 2005/0251257 A1 | 11/2005 | Mitchell et al. | |
| 2005/0261768 A1 * | 11/2005 | Trieu | A61B 17/7065 623/17.11 |
| 2006/0041313 A1 | 2/2006 | Allard et al. | |
| 2006/0093646 A1 | 5/2006 | Cima et al. | |
| 2006/0100705 A1 | 5/2006 | Puno et al. | |
| 2006/0149372 A1 | 7/2006 | Paxson et al. | |
| 2006/0149376 A1 | 7/2006 | Shimp et al. | |
| 2006/0167549 A1 | 7/2006 | Mathys et al. | |
| 2006/0190079 A1 | 8/2006 | Istephanous et al. | |
| 2006/0219661 A1 | 10/2006 | Towse et al. | |
| 2006/0235534 A1 | 10/2006 | Gertzman et al. | |
| 2006/0265065 A1 | 11/2006 | Bagga et al. | |
| 2006/0293748 A1 | 12/2006 | Alexander et al. | |
| 2006/0293752 A1 * | 12/2006 | Moumene | A61F 2/4425 623/17.13 |
| 2007/0010885 A1 | 1/2007 | Liu et al. | |
| 2007/0093898 A1 | 4/2007 | Schwab et al. | |
| 2007/0106298 A1 * | 5/2007 | Carli | A61B 17/7065 606/86 A |
| 2007/0118220 A1 | 5/2007 | Liu et al. | |
| 2007/0118223 A1 | 5/2007 | Allard et al. | |
| 2007/0191958 A1 * | 8/2007 | Abdou | A61B 17/025 623/17.16 |
| 2007/0233247 A1 | 10/2007 | Schwab | |
| 2007/0233248 A1 | 10/2007 | Schwab et al. | |
| 2007/0260320 A1 | 11/2007 | Peterman et al. | |
| 2007/0269475 A1 | 11/2007 | Gil et al. | |
| 2007/0270951 A1 | 11/2007 | Davis et al. | |
| 2007/0270956 A1 | 11/2007 | Heinz | |
| 2007/0282441 A1 | 12/2007 | Stream et al. | |
| 2007/0288028 A1 | 12/2007 | Gorensek et al. | |
| 2007/0293949 A1 | 12/2007 | Salerni et al. | |
| 2008/0014243 A1 | 1/2008 | Ellingsen et al. | |
| 2008/0071380 A1 | 3/2008 | Sweeney | |
| 2008/0077171 A1 | 3/2008 | Blain et al. | |
| 2008/0077246 A1 * | 3/2008 | Fehling | A61F 2/442 623/17.16 |
| 2008/0097610 A1 | 4/2008 | Guyer et al. | |
| 2008/0140203 A1 * | 6/2008 | Davis | A61F 2/442 623/17.13 |
| 2008/0154378 A1 | 6/2008 | Pelo | |
| 2008/0161924 A1 * | 7/2008 | Viker | A61F 2/442 623/17.15 |
| 2008/0195209 A1 | 8/2008 | Garcia et al. | |
| 2008/0221689 A1 | 9/2008 | Chaput et al. | |
| 2008/0249622 A1 | 10/2008 | Gray | |
| 2008/0269764 A1 | 10/2008 | Blain et al. | |
| 2008/0269806 A1 | 10/2008 | Zhang et al. | |
| 2008/0288076 A1 | 11/2008 | Soo et al. | |
| 2009/0005784 A1 | 1/2009 | Blain et al. | |
| 2009/0005871 A1 | 1/2009 | White et al. | |
| 2009/0014243 A1 | 1/2009 | Whigham | |
| 2009/0024132 A1 | 1/2009 | Blain et al. | |
| 2009/0076613 A1 * | 3/2009 | Biedermann | A61F 2/442 623/17.16 |
| 2009/0082819 A1 | 3/2009 | Blain et al. | |
| 2009/0088800 A1 | 4/2009 | Blain et al. | |
| 2009/0088853 A1 | 4/2009 | Ogilvie et al. | |
| 2009/0132048 A1 | 5/2009 | Denzer | |
| 2009/0182432 A1 | 7/2009 | Zdeblick et al. | |
| 2009/0187247 A1 | 7/2009 | Metcalf, Jr. et al. | |
| 2009/0204152 A1 | 8/2009 | Blain | |
| 2009/0234362 A1 | 9/2009 | Blain et al. | |
| 2009/0259316 A1 * | 10/2009 | Ginn | A61B 17/7062 623/17.16 |
| 2009/0264928 A1 | 10/2009 | Blain | |
| 2009/0270992 A1 * | 10/2009 | Gerber | A61F 2/441 623/17.16 |
| 2009/0276049 A1 | 11/2009 | Weiland | |
| 2009/0312837 A1 | 12/2009 | Eisermann et al. | |
| 2010/0076559 A1 | 3/2010 | Bagga et al. | |
| 2010/0094426 A1 | 4/2010 | Grohowski, Jr. et al. | |
| 2010/0121385 A1 | 5/2010 | Blain et al. | |
| 2010/0173264 A1 | 7/2010 | Fredriksson et al. | |
| 2010/0204798 A1 | 8/2010 | Gerbec et al. | |
| 2010/0218854 A1 | 9/2010 | Garcia Saban et al. | |
| 2010/0228288 A1 | 9/2010 | Blain | |
| 2010/0249937 A1 | 9/2010 | Blain et al. | |
| 2010/0274286 A1 | 10/2010 | Blain et al. | |
| 2010/0274358 A1 | 10/2010 | Mueller et al. | |
| 2010/0303722 A1 | 12/2010 | Jin et al. | |
| 2011/0009965 A1 | 1/2011 | Ankem | |
| 2011/0040301 A1 | 2/2011 | Blain et al. | |
| 2011/0082503 A1 | 4/2011 | Blain | |
| 2011/0190902 A1 | 8/2011 | Tong et al. | |
| 2011/0224796 A1 | 9/2011 | Weiland et al. | |
| 2011/0230970 A1 | 9/2011 | Lynn et al. | |
| 2011/0233169 A1 | 9/2011 | Mayfield et al. | |

(56) References Cited

U.S. PATENT DOCUMENTS

| | | |
|---|---|---|
| 2011/0282454 A1 | 11/2011 | Ullrich, Jr. et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wenzel |
| 2012/0149991 A1 | 6/2012 | Blain et al. |
| 2012/0158056 A1 | 6/2012 | Blain |
| 2012/0158144 A1 | 6/2012 | Ullrich, Jr. et al. |
| 2012/0172991 A1 | 7/2012 | Bertele et al. |
| 2012/0232664 A1 | 9/2012 | Ulrich, Jr. et al. |
| 2012/0239150 A1 | 9/2012 | Ullrich, Jr. et al. |
| 2012/0239151 A1 | 9/2012 | Ulrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |
| 2013/0096689 A1* | 4/2013 | Lowry ............... A61B 17/7055 623/17.16 |
| 2013/0123925 A1 | 5/2013 | Patterson et al. |
| 2013/0166030 A1* | 6/2013 | Biedermann ........... A61F 2/442 623/17.16 |
| 2013/0310883 A1 | 11/2013 | Levy et al. |
| 2014/0018924 A1 | 1/2014 | McManus et al. |

FOREIGN PATENT DOCUMENTS

| | | |
|---|---|---|
| EP | 1449544 | 8/2004 |
| EP | 2386274 | 11/2011 |
| JP | 08010276 | 1/1996 |
| JP | 19968010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004008983 | 1/2004 |
| WO | 2004041131 | 5/2004 |
| WO | 2006081843 | 8/2006 |
| WO | 2006116306 | 11/2006 |
| WO | 2006119088 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |
| WO | 2011094748 | 8/2011 |

OTHER PUBLICATIONS

Astra Tech Dental, "Nanolevel topographic modifications on the OsseoSpeed surface", http://shop.dentsplyimplants.us, Mar. 8, 2001.

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growith of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Pending U.S. Appl. No. 13/286,813 of Chad J. Patterson, et al. filed Nov. 1, 2011.

Pending U.S. Appl. No. 13/713,417 of Chad J. Patterson, et al. filed Dec. 13, 2012.

Pending U.S. Appl. No. 13/784,144 of Peter F. Ullrich, Jr., et al. filed Mar. 4, 2013.

Pending U.S. Appl. No. 13/826,304 of Peter F. Ullrich, Jr., et al. filed Mar. 14, 2013.

Supplementary Partial European Search Report issued Aug. 19, 2011, for EP 06 75 9086.

Supplementary Partial European Search Report issued Sep. 27, 2011, for EP 06 75 9086.

Variola, et al., "Nanoscale surface modifications of medically relevant metals: state-of-the art and prespectives", Nanoscale, 2011, 3, 335-353.

Wennerberg, A., et al., "Effects of titanium surface topography on bone integration: a systematic review", Clin. Oral Impl. Res., 20 (Suppl. 4), 2009, pp. 172-184.

Wennerberg, et al., "Spontaneously formed nanostructures on titanium surfaces", Clin. Oral Impl. Res., 2012, 1-7.

* cited by examiner

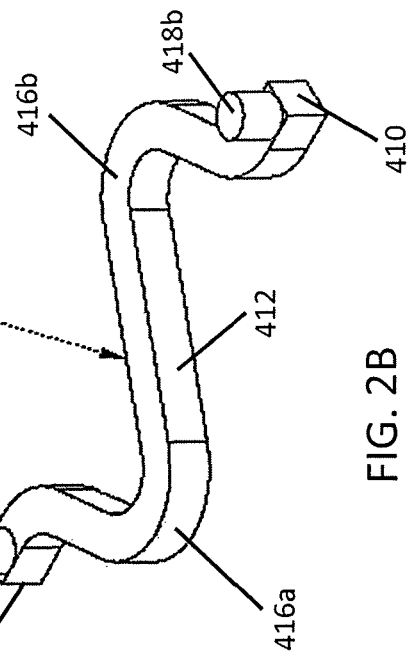
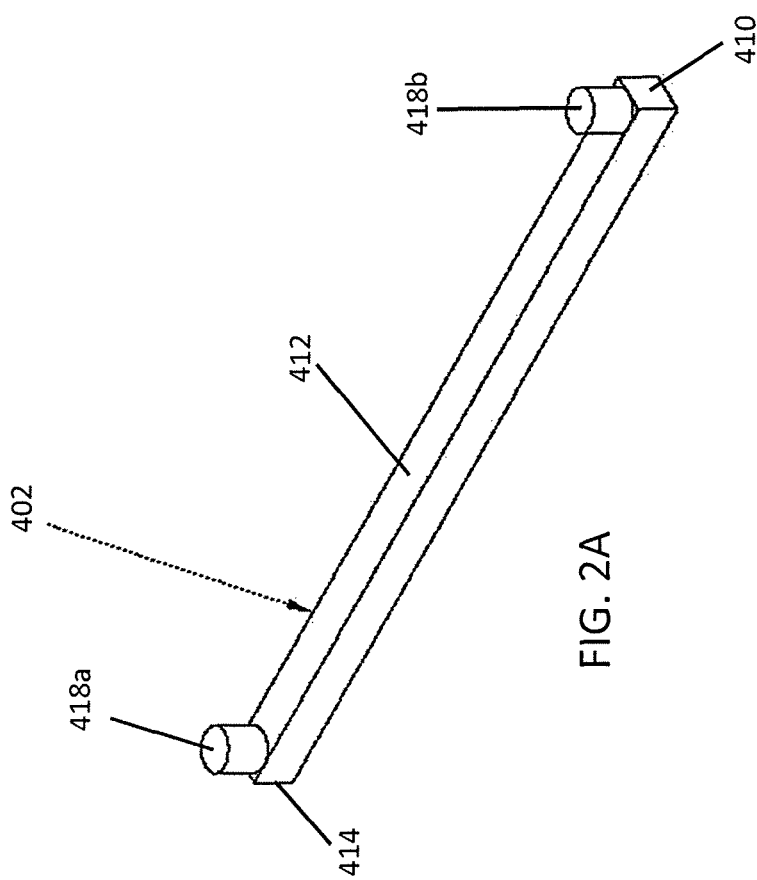

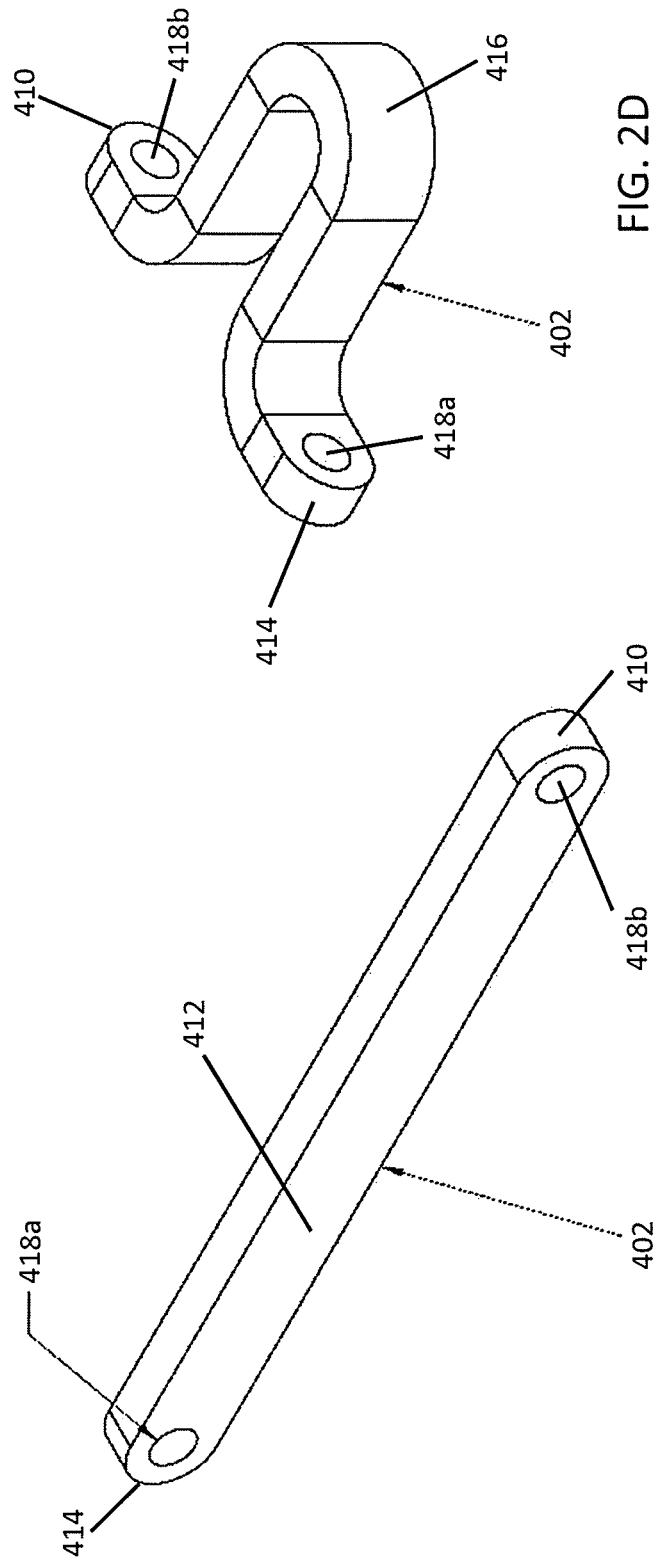

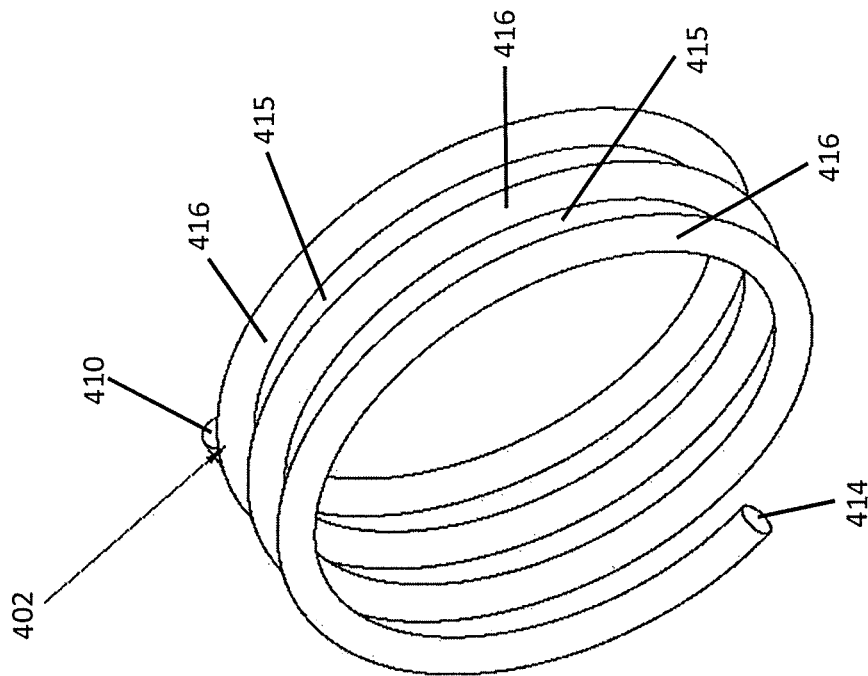
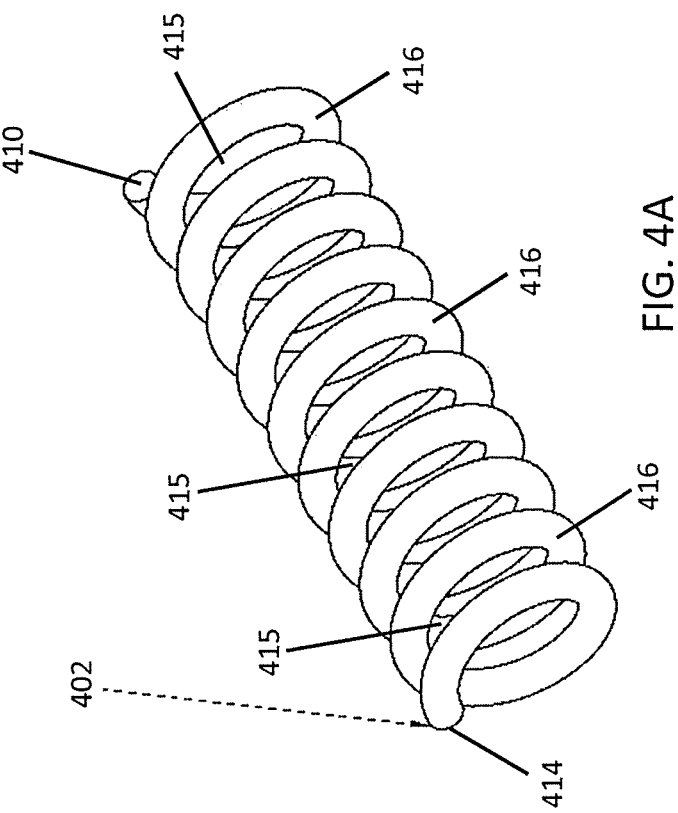

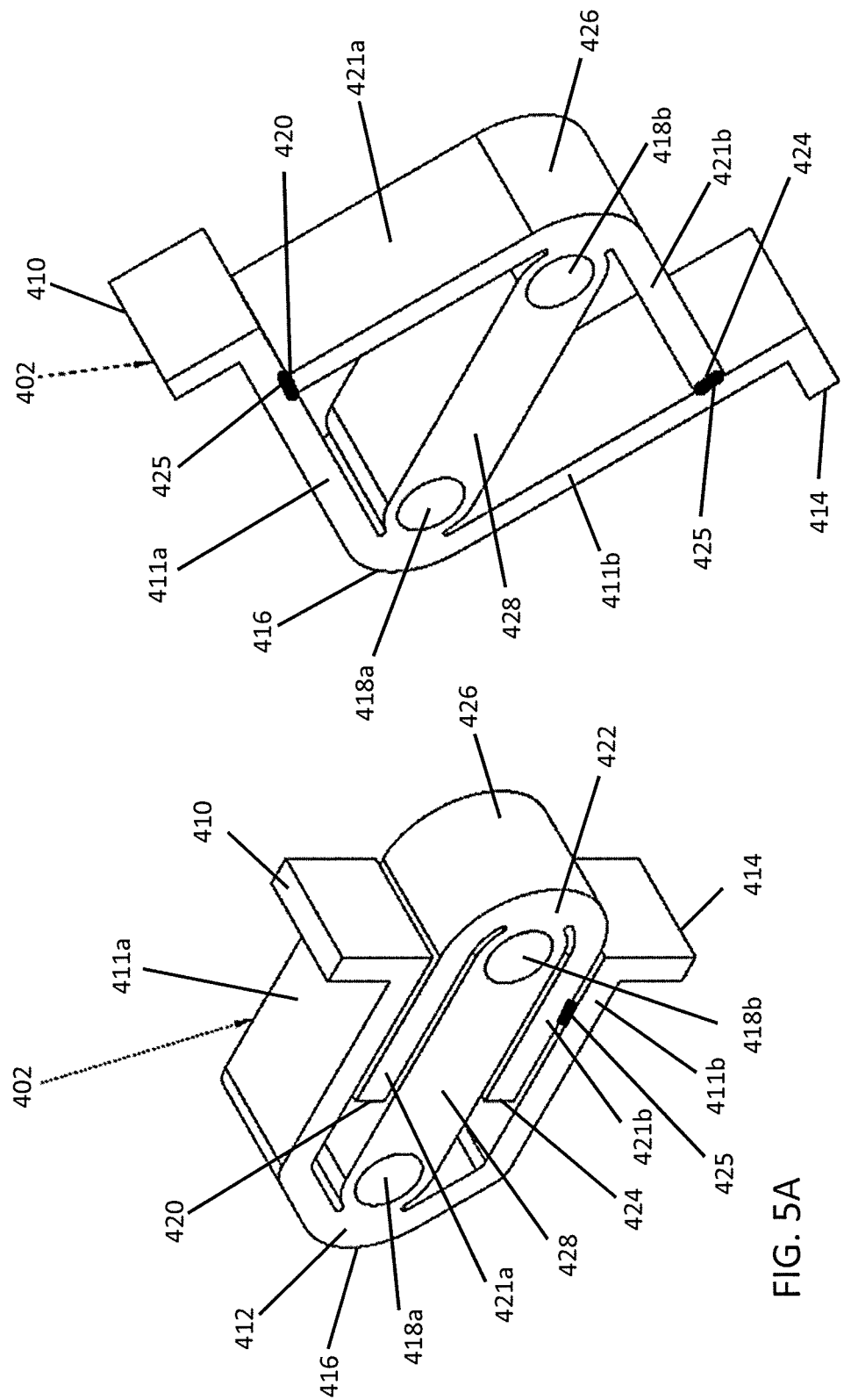

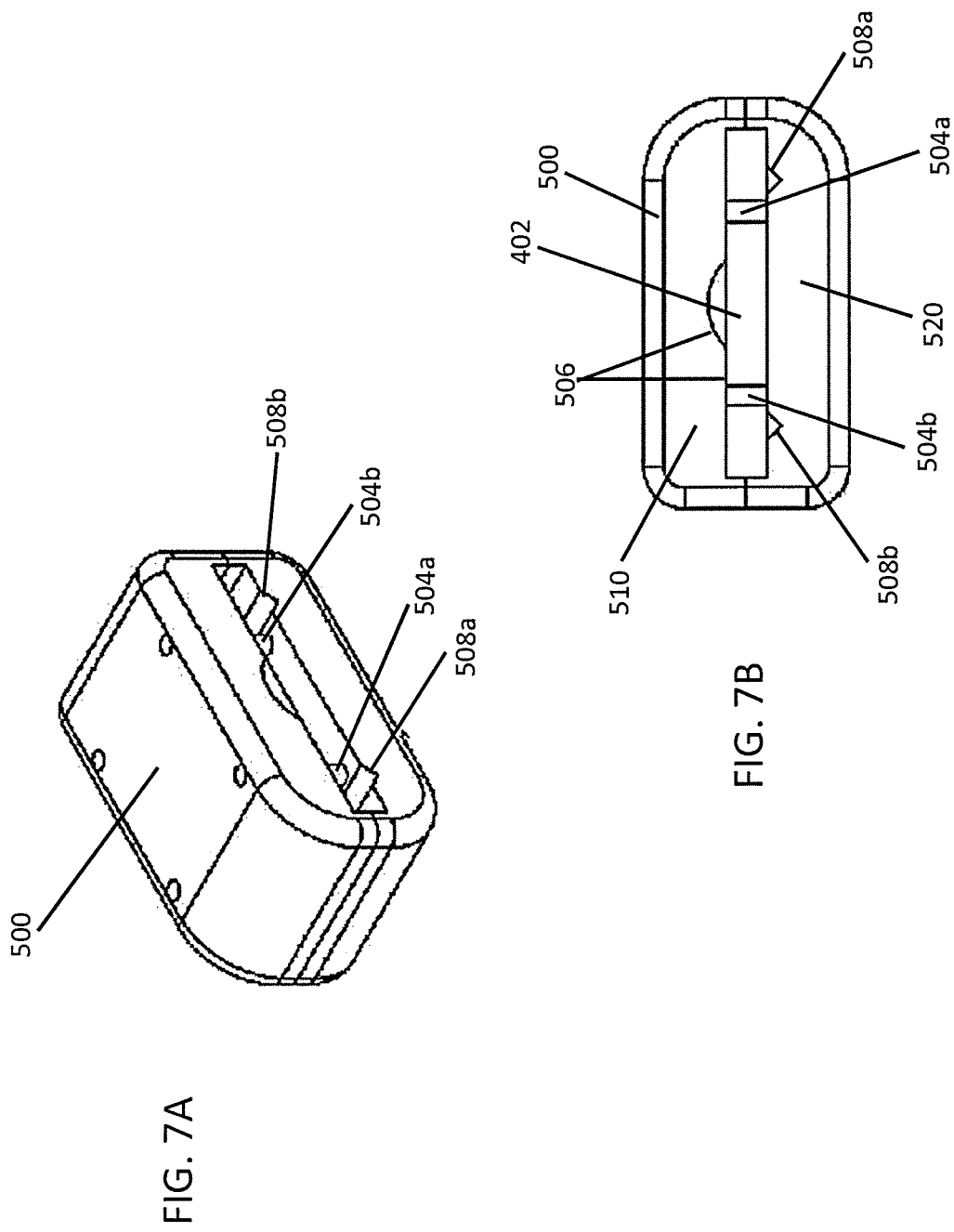

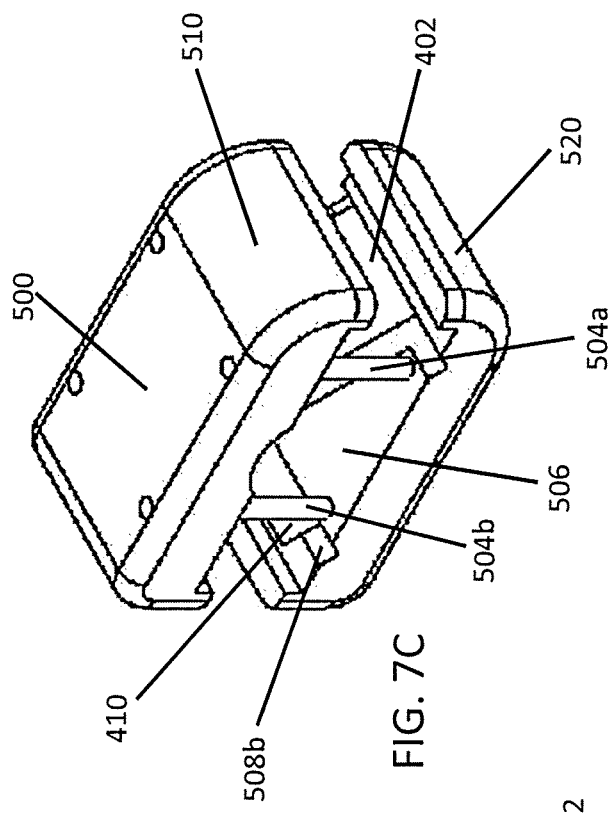
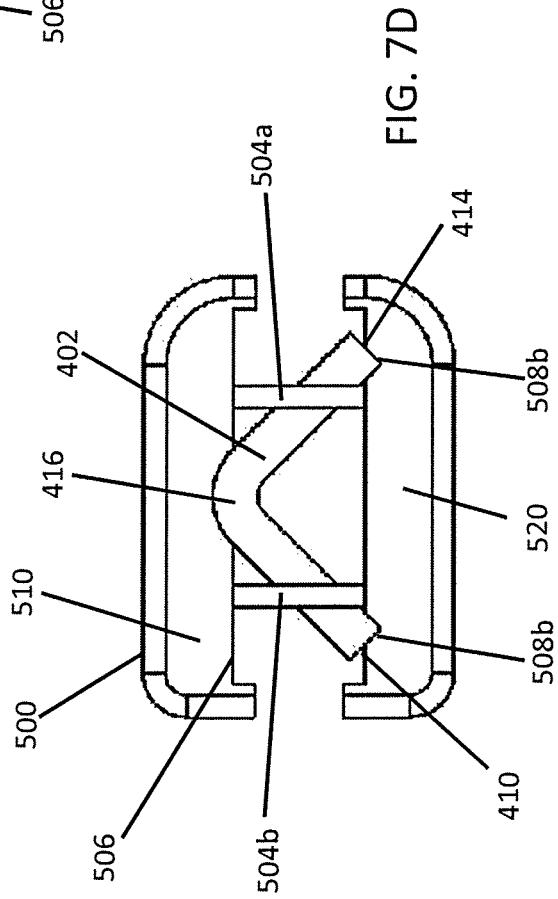
FIG. 7C
FIG. 7D

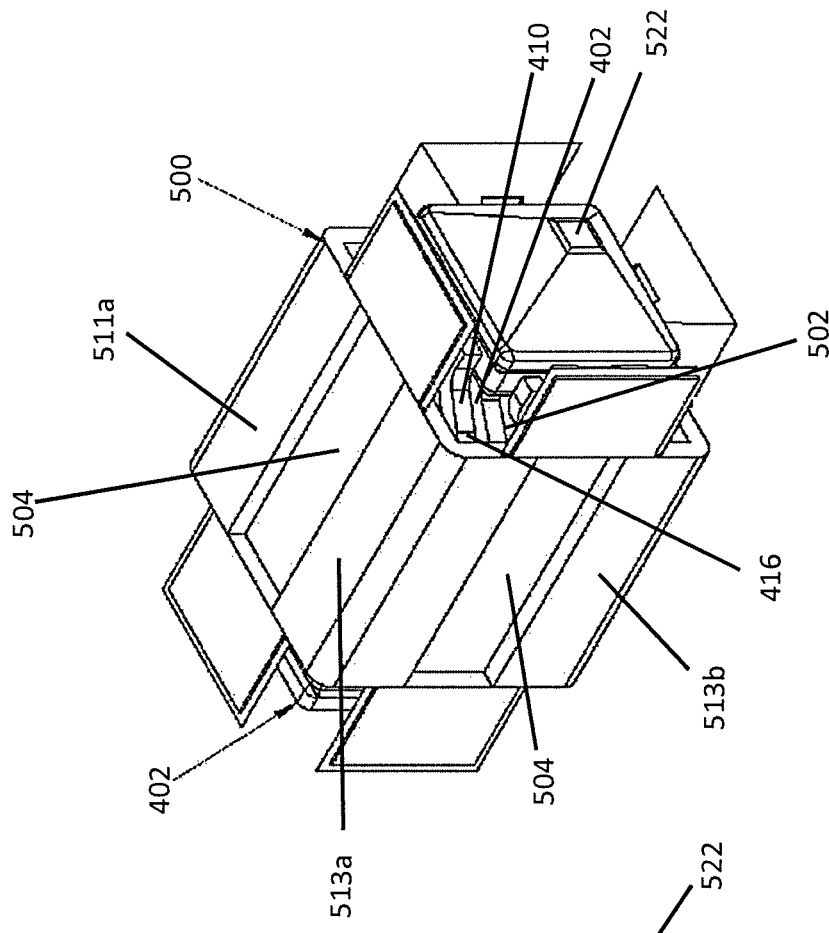
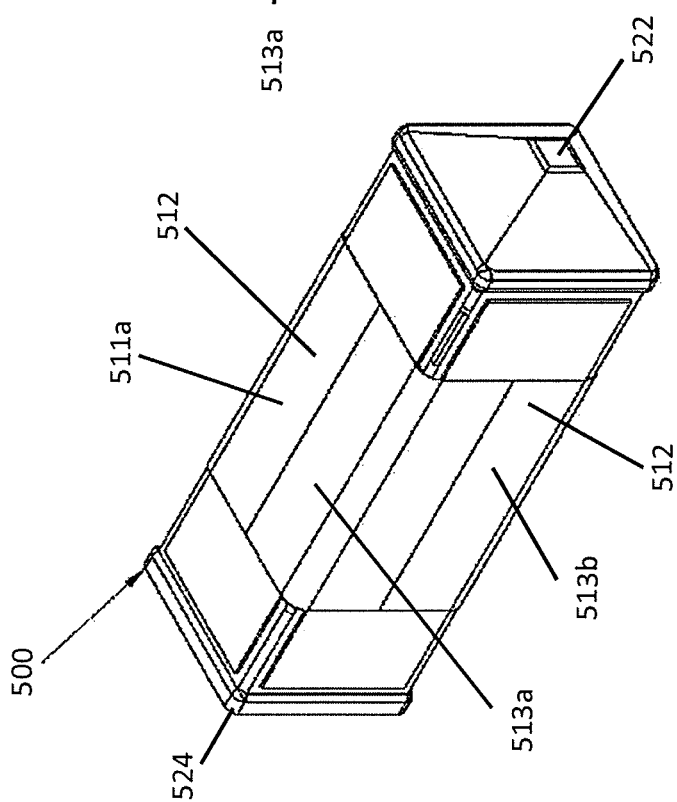
FIG. 8B
FIG. 8A

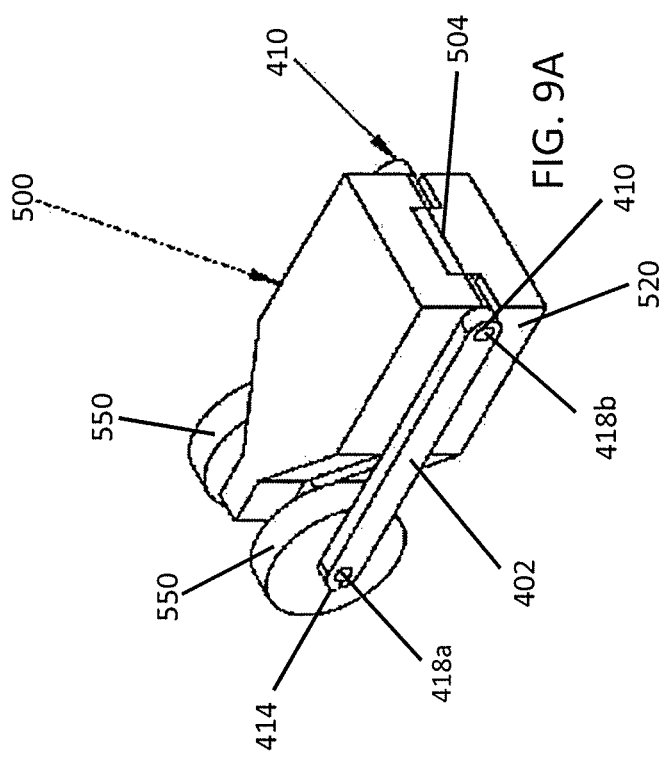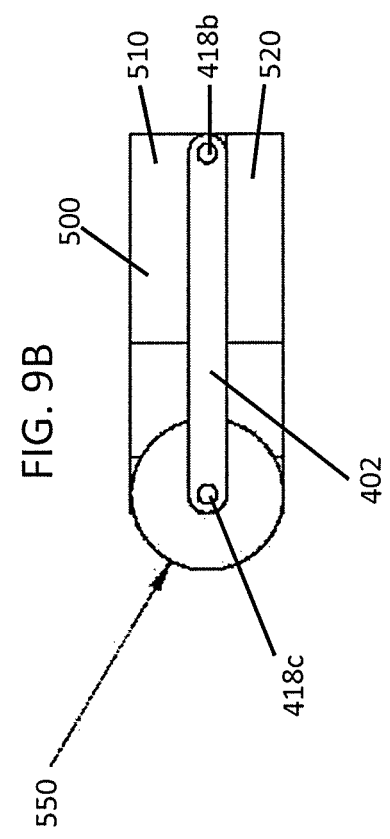

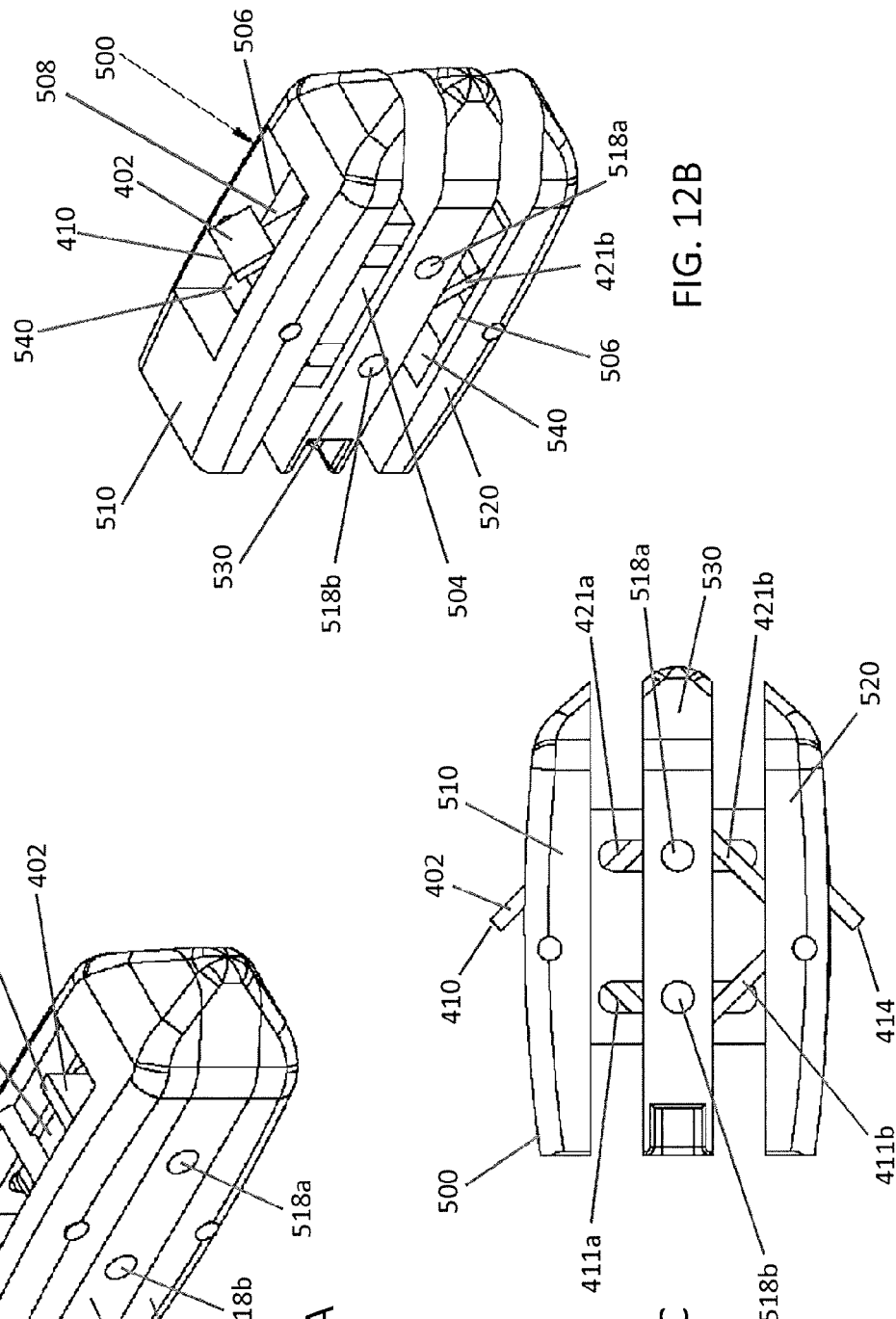

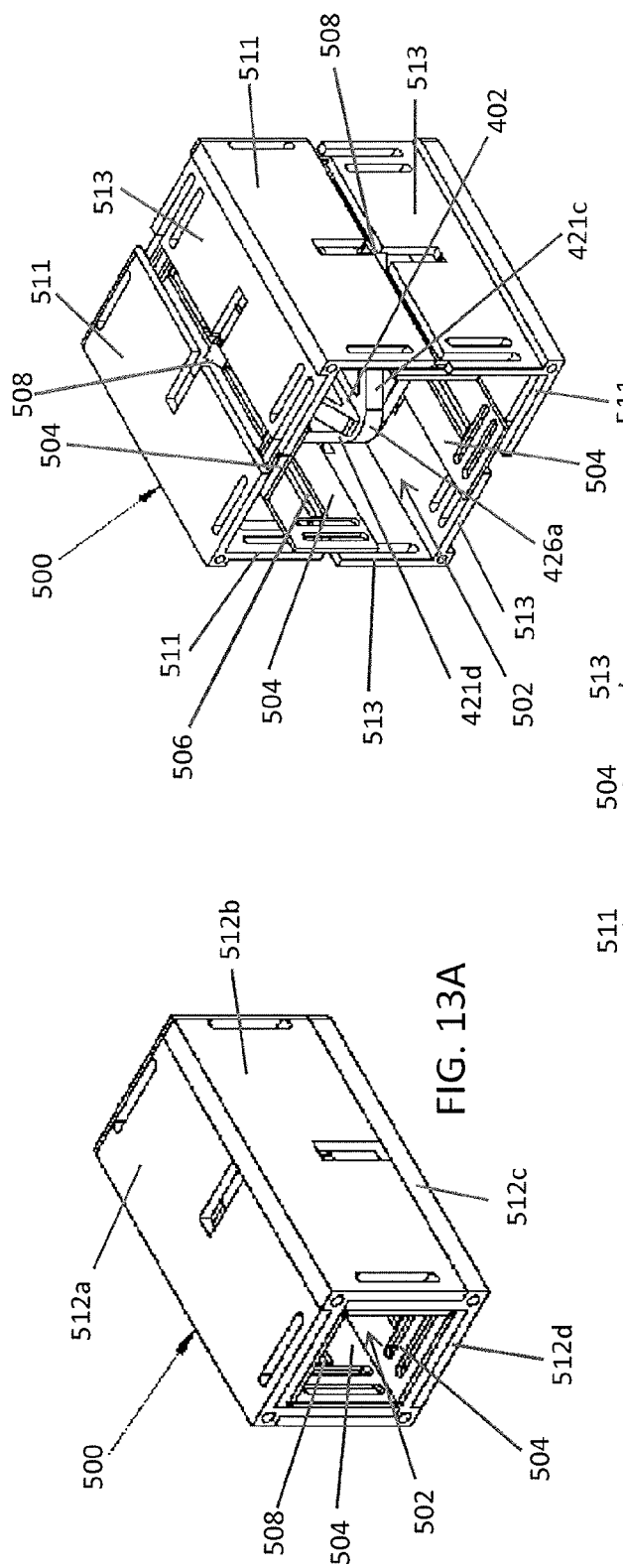
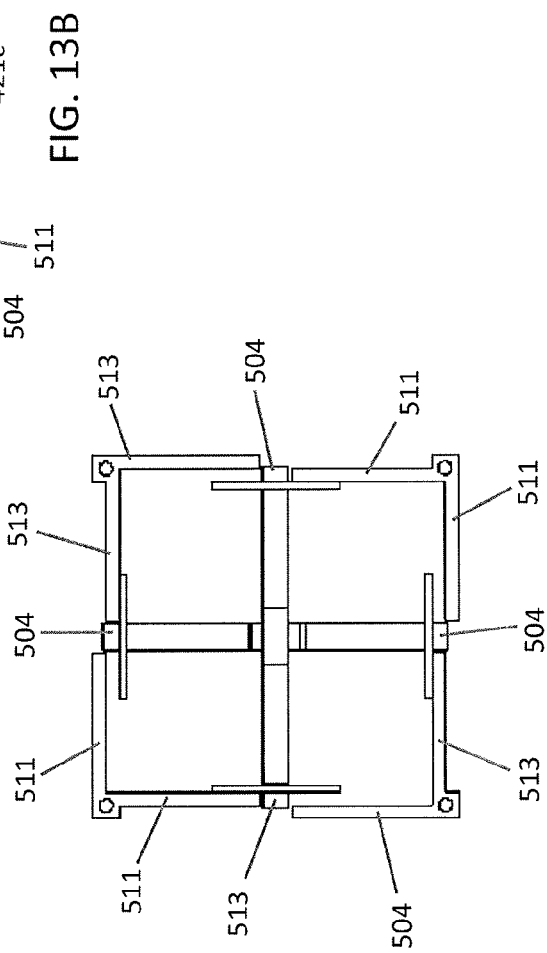
FIG. 13A
FIG. 13B
FIG. 13C

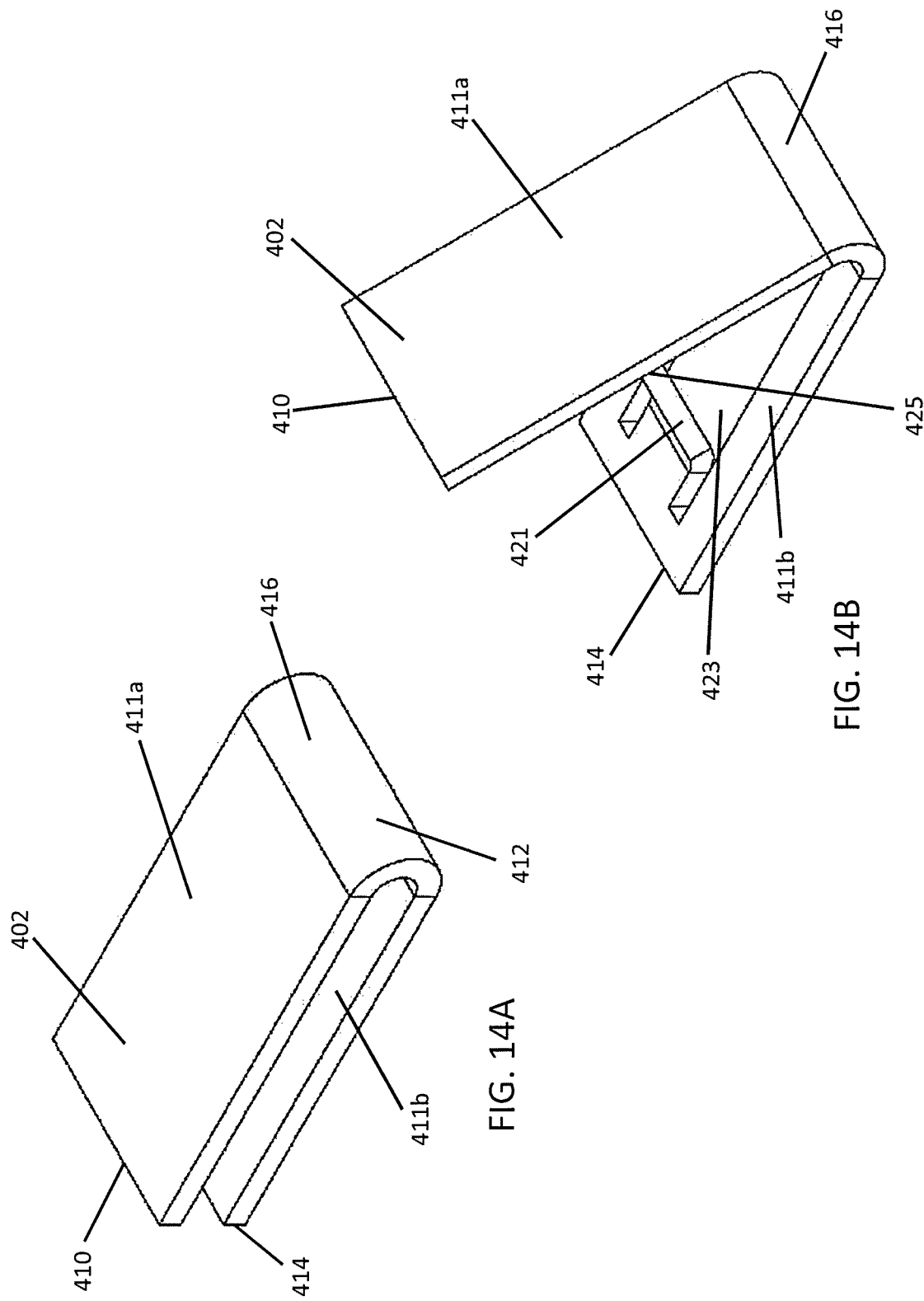

THERMALLY ACTIVATED SHAPE MEMORY SPRING ASSEMBLIES FOR IMPLANT EXPANSION

FIELD OF THE INVENTION

The invention relates generally to springs for expansion of implants, especially spinal implants. In particular, the invention relates to springs comprising a material that has a thermal shape memory, which expand or conform to a predetermined shape at body temperature, as well as methods of using implants comprising such springs, including for spinal fusion applications.

BACKGROUND OF THE INVENTION

Various publications, including patents, published applications, technical articles and scholarly articles are cited throughout the specification. Each of these cited publications is incorporated by reference herein, in its entirety and for all purposes.

Orthopedic implants come in many different shapes and sizes to accommodate different sizes and needs of particular patients. For implantation, an incision at or near the site of implantation, or otherwise conducive for implantation, is made in the patient, with additional tissue dissected to create a pathway for guiding the implant to its ultimate location within the body. Larger and more irregularly shaped implants generally necessitate larger incisions and larger pathway dissections, causing additional trauma to the patient's body and risking unintended injury to the patient. In addition, such larger incisions and tissue dissection increases the risk of an infection, prolongs recovery time, and may cause additional discomfort in the patient during the post-surgery healing period.

It is desirable to minimize trauma to the body during the implantation procedure, yet there are practical limitations to these efforts insofar as the implant needs sufficient room for insertion and placement. More recently, expandable implants have emerged. These expandable implants benefit patients by requiring much smaller incisions and dissection pathways, thereby improving patient healing time and reducing discomfort.

Expandable implants currently in use rely upon manipulation during the surgical procedure. Often, this manipulation requires significant amounts of time for adjusting the implant until the final extended position is attained. The additional time required for this process increases cost of the procedure, as well as enhances the risk to the patient for developing an infection or other complications. Thus, there is a give and take in terms of reducing surgical manipulation in one part of the implantation procedure, but increasing surgical manipulation in another part of the implantation procedure Therefore, there remains a need in the art for implantation procedures that minimize surgical manipulation both in terms of the extent of incision and dissection required, and in terms of placement and positioning of the implant at the implantation site. It is believed that improvements in the design of expandable implants themselves can facilitate improvement in implantation procedures.

SUMMARY OF THE INVENTION

The invention features expandable implants, preferably for implantation in a human body. In some aspects, the expandable implants comprise a top portion and a bottom portion that are not connected to each other and are each independently operably connected to at least one movable joint that facilitates movement of at least one of the top portion and the bottom portion away from the other portion, and comprise at least one thermal memory spring operably connected to the implant. The thermal memory spring comprises a thermal memory material that is activated to expand the spring into a pre-established thermal memory shape or state when heated to a temperature that transitions the thermal memory spring from its compact shape or state to its activated or expanded shape or state. The material may be nitinol or an alloy thereof that has thermal memory properties. The transition temperature is preferably a temperature at or above about 37 degrees C. When the spring reaches the transition temperature, the spring expands into a pre-established thermal memory shape or state, and this expansion moves at least one of the top portion and the bottom portion of the implant away from the other portion to expand the implant.

The upper portion and/or the bottom portion of the implant may comprise undercuts, preferably on a surface of the upper portion and/or bottom portion that is internal to the implant, which undercuts house the thermal memory spring within the implant. The upper portion and/or the bottom portion of the implant may comprise one or more sockets, preferably on a surface of the upper portion and/or bottom portion that is internal to the implant, into which the ends of the thermal memory spring or an arch formed as part of the pre-established thermal memory shape embed when the thermal memory spring expands into the pre-established thermal memory shape. Embedding of the spring into such sockets locks the implant in an expanded state.

In some aspects, the expandable implants comprise a plurality of sidewalls that are not connected to each other and are each independently operably connected to at least one movable joint that facilitates movement of at least one sidewall away from an adjacent sidewall or adjacent sidewalls, and comprise at least one thermal memory spring operably connected to the implant. The thermal memory spring comprises a thermal memory material that is activated to expand the spring into a pre-established thermal memory shape or state when heated to a temperature that transitions the thermal memory spring from its compact shape or state to its activated or expanded shape or state. The material may be nitinol or an alloy thereof that has thermal memory properties. The transition temperature is preferably a temperature at or above about 37 degrees C. When the spring reaches the transition temperature, the spring expands into a pre-established thermal memory shape or state, and this expansion moves at least one sidewall away from the adjacent sidewall(s) to expand the implant.

One or more of the sidewalls of the implant may comprise undercuts, preferably on a surface of the sidewalls that is internal to the implant, which undercuts house the thermal memory spring within the implant. One or more of the sidewalls of the implant may comprise one or more sockets, preferably on a surface of the sidewalls that is internal to the implant, into which the ends of the thermal memory spring or an arch formed as part of the pre-established thermal memory shape embed when the thermal memory spring expands into the pre-established thermal memory shape. Embedding of the spring into such sockets locks the implant in an expanded state.

In some aspects, the expandable implants comprise a top portion and a bottom portion that are not connected to each other, and at least one of the top portion and the bottom portion are operably connected to at least one thermal memory spring. The thermal memory spring comprises a thermal memory material that is activated to expand the spring into a pre-established thermal memory shape or state when heated to a temperature that transitions the thermal memory spring from its compact shape or state to its activated or expanded shape or state. The material may be nitinol or an alloy thereof that has thermal memory properties. The transition temperature is preferably a temperature at or above about 37 degrees C. When the spring reaches the transition temperature, the spring expands into a pre-established thermal memory shape or state, and this expansion moves at least a section of the top portion away from at least a section of the bottom portion to expand the implant.

The upper portion and/or the bottom portion of the implant may comprise undercuts, preferably on a surface of the upper portion and/or bottom portion that is internal to the implant, which undercuts house the thermal memory spring within the implant. The upper portion and/or the bottom portion of the implant may comprise one or more sockets, preferably on a surface of the upper portion and/or bottom portion that is internal to the implant, into which the ends of the thermal memory spring or an arch formed as part of the pre-established thermal memory shape embed when the thermal memory spring expands into the pre-established thermal memory shape. Embedding of the spring into such sockets locks the implant in an expanded state. The upper portion and/or the bottom portion of the implant may each be independently operably connected to a hinge. The at least one thermal memory spring may be operably connected to at least one expansion roller that facilitates movement of at least a section of the top portion away from at least a section of the bottom portion to expand the implant. In some embodiments, the expansion roller embeds into the undercuts or sockets, thereby locking the expansion roller in place between the upper portion and the bottom portion when the thermal memory spring expands into the pre-established thermal memory shape.

In some aspects, a portion of the thermal memory spring, for example, the first end and/or the second end may expand outside of the implant, and contact a bone surface proximal to the implant surface, thereby providing for or otherwise enhancing anti-migration or anti expulsion of the implant. Portions of the expanded thermal memory spring may contact bone surfaces, and embed into the bone, thereby reducing or eliminating undesired re-positioning, movement, or expulsion of the implant. Thus, the expanded thermal memory spring may comprise anti-expulsion edges or features. Any of the thermal memory springs described or exemplified herein may comprise anti-expulsion edges or features.

In accordance with any of the implants, the thermal memory spring may comprise a pre-established thermal memory shape that includes at least one arch. The at least one arch may be located substantially in the middle of the thermal memory spring. The thermal memory spring may comprise a pre-established thermal memory shape that includes at least two arches. The thermal memory spring may comprise a pre-established thermal memory shape that includes a plurality of arches. In some aspects, a slot is present between each arch. The thermal memory spring may comprise at least one spring arm and at least one truss arm, and in some aspects may comprise a plurality of spring arms and a plurality of truss arms. When the thermal memory spring expands into the pre-established thermal memory shape or state, the at least one or plurality of truss arm(s) extend(s) outward until an end of the at least one or plurality of truss arm(s) embed(s) in a notch on an internal surface of the at least one or plurality of spring arm(s). Embedding of the truss arm end(s) into the notch locks each spring arm in a pre-established thermal memory position. The thermal memory spring may comprise a solenoid shape, including a plurality of arches, with each arch being separated from an adjacent arch by a slot. The solenoid-shaped spring may comprise one or more expansion arm, which extend from at least one of the ends of the spring.

Methods of implanting the implants in a patient are provided, which include implanting a thermal memory spring-containing implant in a patient. The implants are inserted into the patient, then placed and positioned within the desired location of implantation, and allowed to warm to the temperature at which the thermal memory spring is activated to assume its thermal memory shape and expand the implant. The practitioner may actively warm the implant to facilitate activation of the spring. The implant may be adjusted and re-positioned as necessary after the implant has expanded. Conversely, in some aspects, if the implant is found to be improperly positioned, cooling the device with a medium such as refrigerated saline solution may cause the thermally activated spring to at least partially deactivate and at least partially return to at least a partially contracted shape, making the implant more maneuverable. Due to the properties of Nitinol/Titanium alloys as well as other thermally activated materials, this reversible process can be completed numerous times. Thus, it is preferable that the spring activation and expansion be reversible, but only upon sufficient cooling such that an implant comprising such a spring would not improperly contract into a compact state when implanted within the body. An implant may comprise a bone graft material to facilitate osteointegration of the implant after implantation.

Kits comprising the implants are also provided. Kits comprise at least one implant, at least one thermal memory spring, and instructions for using the implant in a method for implanting the implant. Preferably, the implant is pre-fabricated to include the spring, although in some aspects, the practitioner may insert the spring into the implant.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 2A shows an example of an embodiment of a shape-memory spring in a relaxed state;

FIG. 2B shows an example of the shape-memory spring depicted in FIG. 2A in an activated state, producing two arches;

FIG. 2C shows an alternative embodiment of the shape-memory spring depicted in FIG. 2A, in a relaxed state;

FIG. 2D shows an example of the shape-memory spring depicted in FIG. 2C in an activated state, producing a single arch;

FIG. 4A shows an example of a solenoid-like embodiment of a shape-memory spring in a relaxed state;

FIG. 4B shows an example of the solenoid-like shape-memory spring depicted in FIG. 4A in an activated state;

FIG. 5A shows an example of an embodiment of a shape-memory spring having truss arms in a relaxed state;

FIG. 5B shows an example of the shape-memory spring depicted in FIG. 5A in an activated state, with the truss arms extended into a slot;

FIG. 7A shows an example of the shape-memory spring of FIG. 1A in a relaxed state within an implant that has not expanded;

FIG. 7B shows a side perspective of the implant and spring shown in FIG. 7A;

FIG. 7C shows the shape-memory spring and implant of FIG. 7A, with the spring in an activated state that expands the implant by forcing the top and bottom sections of the implant apart along a movable joint;

FIG. 7D shows a side perspective of the implant and spring shown in FIG. 7C;

FIG. 8A shows an example of an implant that contains a shape-memory spring that has not yet been activated such that the implant is not expanded;

FIG. 8B shows the shape-memory spring and implant of FIG. 8A, with the spring in an activated state that expands the implant;

FIG. 9A shows an example of an implant that has a shape-memory spring attached to a non-expanded implant having an expansion roller;

FIG. 9B shows a side perspective of the implant and spring shown in FIG. 9A;

FIG. 12A shows an example of a non-expanded implant containing a shape-memory spring with truss arms in a relaxed state;

FIG. 12B shows a perspective view of the implant of FIG. 12A with the spring in an activated state that expands the implant;

FIG. 12C shows a side perspective of the implant of FIG. 12A with the spring in an activated state that expands the implant;

FIG. 13A shows an example of a non-expanded implant in which a shape-memory spring with truss arms is present inside in a relaxed state;

FIG. 13B shows a perspective view of the implant of FIG. 13A with the spring in an activated state that expands the implant;

FIG. 13C shows a rear perspective of the implant in an expanded state as shown in FIG. 13B;

FIG. 14A shows an example of an embodiment of a shape-memory spring having an arch in a relaxed state;

FIG. 14B shows an example of the shape-memory spring shown in FIG. 14A in an activated state;

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The invention features mechanisms for expanding implants following their insertion into the body. A foundational feature is an shape-memory spring 402 comprised of a material that has a thermal shape memory. For example, certain metals, including Nitinol (a nickel and titanium alloy) may be shaped into a desired shape or state or configuration at very high temperatures, then forcibly straightened, relaxed, or held in a different shape or state or configuration at room temperature. When the metals are exposed to temperatures greater than room temperature, the metals re-assume the shape or state into which they were formed at the very high temperature, or assume their activated configuration or shape or state. This phenomenon is recognized in the art under various terms, including shape memory, thermal memory, thermal shape memory, and super-elastic memory, and such terms are used interchangeably herein. Accordingly, in some aspects, the invention features shape-memory springs 402.

Preferably, the thermal memory shape of the shape-memory springs 402 described and exemplified herein is assumed at temperatures near body temperature or higher (e.g., 33 degrees C., 34 degrees C., 35 degrees C., 36 degrees C., 37 degrees C., or higher). For example, at room temperature or other temperature below body temperature, the shape-memory springs 402 are in a relaxed state (the shape into which they were forcibly established after creating the desired shape at very high temperatures), but are activated, and expand or otherwise assume their thermal memory shape at body temperature or higher.

Figure 1B:
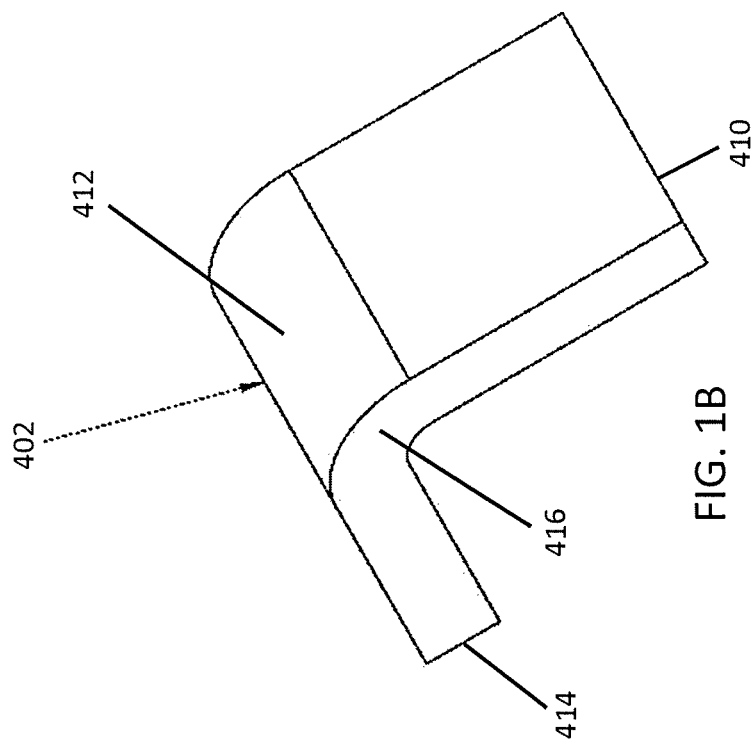
FIG. 1B shows an example of the shape-memory spring depicted in FIG. 1A in an activated state.
Figure 1A:
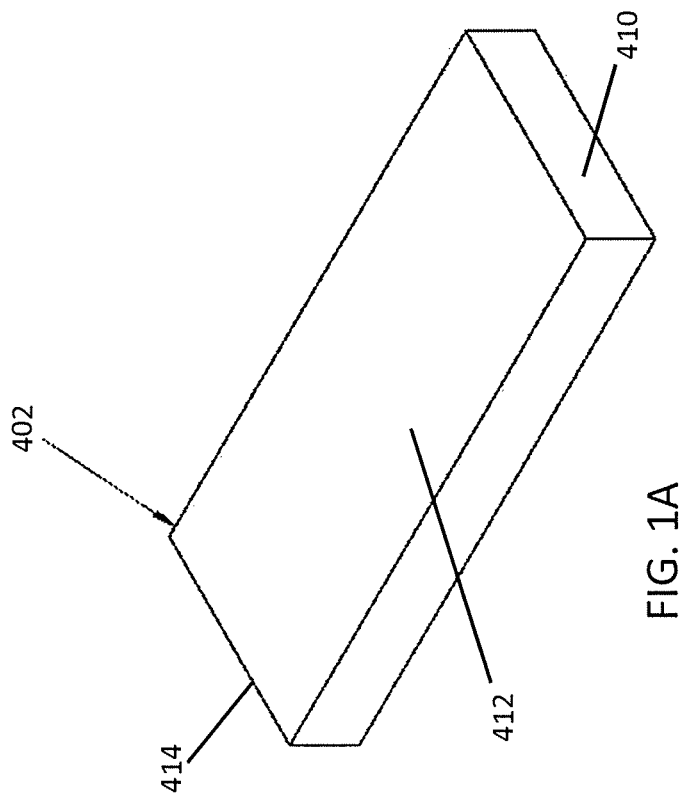
FIG. 1A shows an example of one embodiment of a shape-memory spring in a relaxed state.

In certain aspects, the shape-memory spring 402 comprises a metal with a thermal shape memory. The spring 402 comprises a first end 410, a second end 414, and a mid-section 412 between the first end 410 and second end 414. In some aspects, the spring 402 comprises a rectangular shape, for example, as shown in FIG. 1A, and the spring 402 may lay substantially flat at room temperature (FIG. 1A), and may form at least one arch 416 (FIG. 1B) at elevated temperatures such as body temperature. For example, the spring 402 may comprise an arched thermal memory that is attained when the spring 402 is heated to at least body temperature. The at least one arch 416 occurs within the mid-section 412, and the arch 416 may be substantially in the center of the spring 402 as shown in FIG. 1B or may be off-center, or may be more proximal to the first end 410 and/or the second end 414.

In some aspects, the spring 402 may comprise two arches 416a and 416b at the activation temperature, as shown in FIG. 2B. In the embodiment shown in FIGS. 2A through 2D, the spring 402 may comprise a narrower width relative to the embodiment shown in FIGS. 1A and 1B. The spring 402 may comprise a plurality of arches 416, including any suitable number of arches 416. Three, four, five, six, seven, eight, or more arches 416 are contemplated. Any one or more of the edges, including all of the edges, of the spring 402 may be rounded, radiused, mitered, blunted, or sharp. As shown in FIG. 2A and FIG. 2C, the shape-memory spring 402 may be rectangular, yet relatively narrow in its width and substantially flat or straight at temperatures below the activation temperature, and then assume one arch 416 (e.g., FIG. 2D), or a plurality of arches 416a, 416b, as shown in FIG. 2B at the activation temperature.

The spring 402 may optionally comprise one or more connectors 418, which may facilitate connection of the spring 402 to another structure, including an implant 500 (discussed in more detail below). As shown in FIGS. 2A and 2B, for example, the spring 402 may comprise two connectors 418a and 418b, which may be posts 418a and 418b, and which may be located proximate to the first end 410 and second end 414. As shown in FIGS. 2C and 2D, for example, the connectors 418a and 418b may comprise holes 418a and 418b in some aspects, which may be located proximate to the first end 410 and second end 414.

Figure 3B:
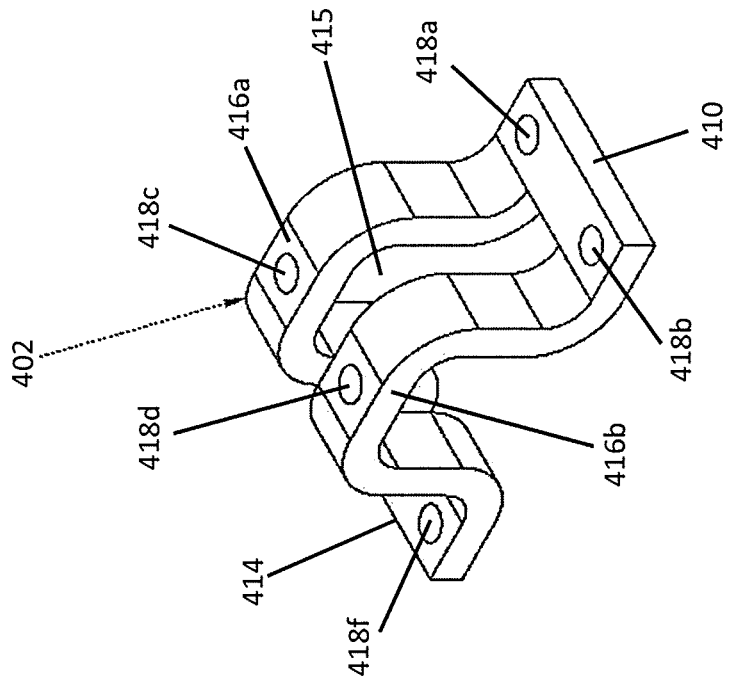
FIG. 3B shows an example of the shape-memory spring depicted in FIG. 3A in an activated state, producing two arches separated by a slot.
Figure 3A:
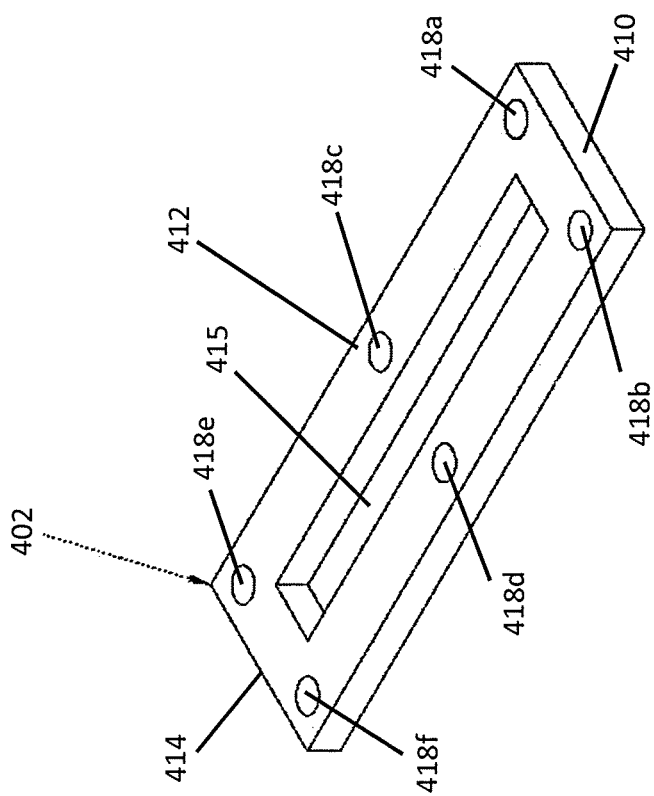
FIG. 3A shows an example of an embodiment of a shape-memory spring having a slot, in a relaxed state.

In some aspects, the spring 402 comprises at least one slot 415 in the mid-section 412, for example, as shown in FIG. 3A and FIG. 3B. Thus, when the spring 402 assumes its thermal memory shape (FIG. 3B), the spring 402 comprises two or more arches 416a and 416b, which are separated by the slot 415 between them. FIGS. 3A and 3B also show the spring 402 as comprising a plurality of connectors 418a-f, which may be a plurality of holes 418a-f (e.g., FIG. 3A and 3B) or posts 418a-f (not shown). The slot 415 may be substantially in the center of the spring 402, but may also be positioned more proximal to the ends 410 or 414, or the sides.

Figure 4D:
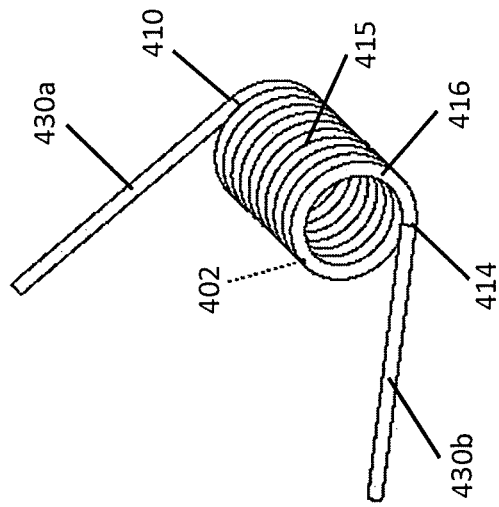
FIG. 4D shows an example of the shape-memory spring depicted in FIG. 4C in an activated state.
Figure 4C:
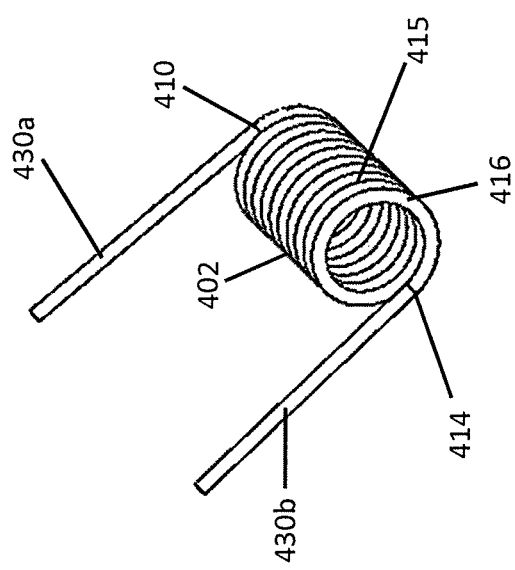
FIG. 4C shows an example of an another embodiment of a solenoid-like shape-memory spring with extension arms in a relaxed state.

In some embodiments, the spring 402 comprises a solenoid or coil shape, for example, as shown in FIG. 4A and FIG. 4B or in FIG. 4C and FIG. 4D. The coiled spring 402 comprises a plurality of arches 416 and a plurality of slots 415 between the arches 416. In some aspects, when the spring 402 assumes its thermal memory shape (FIG. 4B), the arches 416 expand, thereby enlarging the coil diameter. In some aspects, the coiled spring 402 may optionally comprise a first extension arm 430a, extending off of the first end 410 and a second extension arm 430b, extending off of the second end 414 (FIG. 4C). These extension arms 430a, 430b may comprise a separate structure connected to the first end 410 and second end 414, or may simply be non-coiled portions of the spring 402. When the spring 402 assumes its thermal memory shape (FIG. 4D), the first extension arm 430a and/or the second extension arm 430b extend in a different direction, whether upward, downward, outward, or inward from their relaxed direction. In such embodiments, the arches 416 do not expand outward (FIG. 4D), although in some aspects, the arches 416 do expand (in addition to the first extension arm 430a and/or the second extension arm 430b) in a manner similar to that shown in FIG. 4B.

In some aspects, the spring 402 comprises a plurality of arms. For example, as shown in FIG. 5A and FIG. 5B, the spring 402 may comprise a first spring arm 411a and a second spring arm 411b, which are between the first end 410 and second end 414, with the arch 416 between the first spring arm 411a and second spring arm 411b. Each spring arm 411a, 411b may include bends. For example, as shown in FIG. 5A and FIG. 5B, each spring arm 411a,411b bends at substantially a right angle outward and near the first end 410 and second end 414. The spring 402 may also include one or more truss arms 421a,421b. The first truss arm 421a may comprise a first truss arm end 420, and the second truss arm 421b may comprise a second truss arm and 424. The truss arms 421a,421b are also comprised of a thermal memory material, which preferably is the same thermal memory material out of which the remainder of the spring 402 is comprised. The truss arms 421a,421b may form a truss arch 426 near the mid-section 422 between the truss arm ends 420 and 424. The truss arms 421a,421b may be connected to a bridge 428, which may be operably connected to the spring arch 416 and truss arch 426, as shown in FIG. 5A and FIG. 5B. The bridge 428 may, but need not be substantially near the mid-section 412 of the spring 402 and the mid-section 422 of the truss structure. The bridge 428 may optionally comprise one or more connectors 418a, 418b such as the holes 418a, 418b shown on FIG. 5A and FIG. 5B. The one or more connectors 418a,418b may comprise posts 418a,418b (not shown).

When the spring 402 shown in FIG. 5A is activated (e.g., at elevated temperatures), the truss arms 421a,421b extend or expand. The extension or expansion of the truss arms 421a, 421b may facilitate or force the first spring arm 411a and/or second spring arm 411b in their respective extension or expansion, though in some aspects, the truss arms 421a, 421b do not exert any force on the spring arms 411a, 411b. The ends 420 and 424 of the truss arms 421a, 421b may extend along an internal surface of the first spring arm 411a and second spring arm 411b until they reach a notch 425 present on the internal surface of the spring arms 411a, 411b. The ends 420a and 424 slide or otherwise embed into/within the notch 425 and in doing so, become locked in place. When the ends 420a and 424 are locked into the notch 425, each spring arm 411a,411b becomes locked in its pre-established thermal memory position, and the activated spring 402 assumes an expanded state.

Figures 6A, 6B:
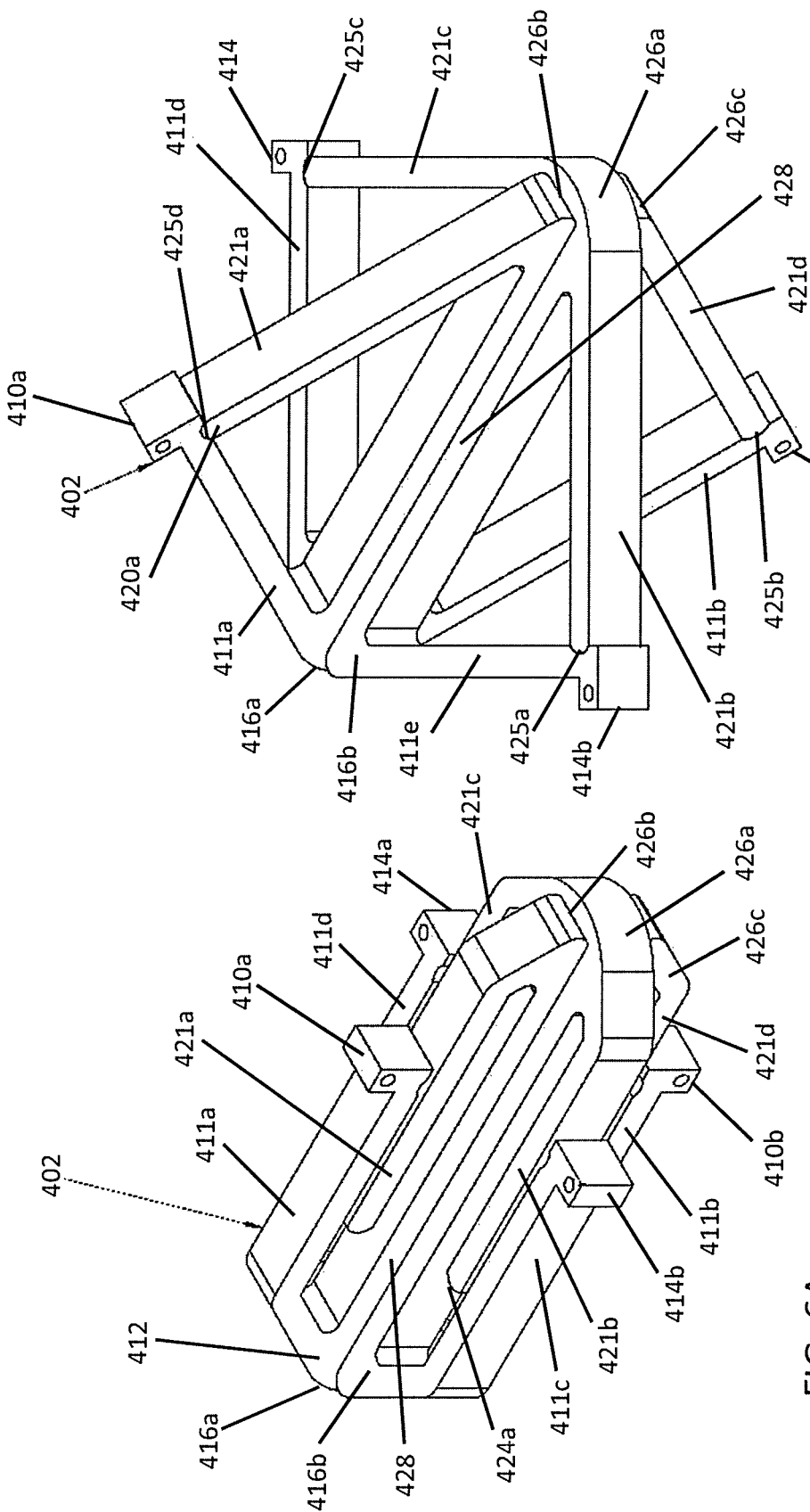
FIG. 6A shows an example of an embodiment of a multi-armed shape-memory spring in a relaxed state.
FIG. 6B shows an example of the multi-armed shape-memory spring depicted in FIG. 6A in an activated state.

In another embodiment, for example, as shown in FIG. 6A and FIG. 6B, the spring 402 may comprise a first spring arm 411a, a second spring arm 411b, a third spring arm 411c, and a fourth spring arm 411d, which are between sets of the first end 410a,410b and the second end 414a,414b, and the spring arms 411a-411d may bend at substantially a right angle outward near the first end 410*a*,410*b* and second end 414*a*, 414*b* (FIG. 6A and FIG. 6B). The spring 402 may also include a plurality of truss arms 421*a*,421*b*,421*c*,421*d* comprised of a thermal memory material, preferably the same material out of which the remainder of the spring 402 is comprised, and forming a plurality of truss arches 426*a*, 426*b*,426*c*.The truss arms 421*a*-421*b* may be connected to a bridge 428, which may be operably connected to the spring arches 416*a*-*d*,and the bridge 428 may be located substantially near the mid-section 412 of the spring 402. The bridge 428 may optionally comprise one or more connectors 418 (not shown in FIGS. 6A and 6B), including posts or holes.

When the spring 402 shown in FIG. 6A is activated (e.g., at elevated temperatures), the truss arms 421*a*-*d* extend outward, thereby facilitating or forcing the first spring arm 411*a*, second spring arm 411*b*,third spring arm 411*c*,and fourth spring arm 411*d* outward, or expanding along with the spring arms 411*a*-*d*.The ends 420*a*-*d* and 424*a*-*d* of the truss arms 421*a*-*d* may extend along an internal surface of the first spring arm 411*a*,second spring arm 411*b*,third spring arm 411*c*,and fourth spring arm 411*d* until they reach a notch 425*a*-*d* on the internal surface. The ends 420*a*-*d* and 424*a*-*d* slide into the notches 425*a*-*d* and in doing so, become locked in place. When the ends 420*a*-*d* and 424 are locked into the notches 425*a*-*d,* each spring arm 411*a*-*d* becomes locked in its pre-established thermal memory position, and the activated spring 402 assumes an expanded state.

The various spring 402 embodiments described or exemplified herein have thermal memory properties that may be used, for example, to expand an implant 500. For example, the implant 500 may have a compact and expandable configuration, and may transition from the compact configuration to the expanded configuration by way of the spring 402. The spring 402 may be positioned within an internal compartment of the implant 500, with the spring 402 in its relaxed, non-activated state. When the implant 500 is inserted into the body of a patient, and when the spring 402 reaches a sufficient temperature within the body (e.g., body temperature), the spring 402 activates by expanding or assuming its thermal memory shape. In so doing, the spring 402 forces the implant 500 into its expanded configuration. The spring 402 comprises a compact and expandable configuration (as well as all intermediate expansion distances between the fully compact and fully expanded configurations). At room temperature or other temperature below body temperature, the spring 402 is not activated or expanded, and preferably is in a compact form. At an elevated temperature such as body temperature, the spring 402 assumes its thermal memory shape, which may include expansion and/or re-shaping.

For example, the implant 500 may comprise any interbody spinal implant 500, which may be intended for implantation in the spine as a disc replacement or spinal motion segment replacement, or implantation in the hip, or implantation in the knee, or implantation in the elbow, or implantation in the shoulder, or any other movable joint or load-bearing area of the body. The implant 500 may have any shape or configuration, and it is to be understood that the implant 500 designs shown in the figures of this specification are intended to show operational principles and potential relationships between the spring 402 and the implant 500 for illustration purposes only. That is, the implants 500 shown are not intended to be limiting, do not represent all possible configurations, and do not necessarily represent actual interbody implants 500. The implants 500 may be of any shape, size, and configuration appropriate for the task and location for which they are intended to be implanted, and may expand according to the principles illustrated in the figures.

Implants 500 may be made of a durable material such as stainless steel, stainless steel alloy, titanium, or titanium alloy, but can also be made of other durable materials such as, but not limited to, polymeric, ceramic, and composite materials. For example, in certain aspects, the implant 500 may be comprised of a biocompatible, polymeric matrix reinforced with bioactive fillers, fibers, or both. Certain implants 500 may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally preferred for certain embodiments due to their acceptable, and desirable, strength and biocompatibility. Durable materials also include polymers such as PEEK and ultra-high molecular weight polyethylene (UHMWPE), as well as composites of polymers and metals, including composites of titanium and PEEK.

FIGS. 7A through 7D show an example of an implant 500 in a compact and expanded state, which is mediated by the activation of a thermal memory spring 402. In the example shown, the implant 500 is configured to utilize the spring 402 shown in FIG. 1A and FIG. 1B, although the implant may utilize any spring 402 described or exemplified herein.

The implant 500 preferably is comprised of two primary sections, a top section 510 and a bottom section 520. The top section 510 and bottom section 520 preferably are not directly connected to each other such that they may be separated when the implant 500 expands, as detailed below. The top section 510 and bottom section 520 may be indirectly connected to each other through at least one movable joint 504*a*,504*b* that bridges the top section 510 and bottom section 520 together to form the implant 500. When the implant 500 is not expanded, the at least one movable joint 504*a*,504*b* is/are substantially closed such that the top section 510 and bottom section 520 may contact each other or at least be in close proximity to each other, as shown in FIGS. 7A and 7B. When the implant 500 expands, the at least one movable joint 504*a*,504*b* opens such that the top section 510 and bottom section 520 separate, but do not become detached from the implant 500. The movable joint 504*a*,504*b* is operably connected to each of the top section 510 and bottom section 520. The movable joint 504*a,* 504*b* facilitates separation of the top section 510 and the bottom section 520, and may do so actively, including moving either or both of the top section 510 and the bottom section 520 (e.g., the movable joint 504 may be actuated by the expansion of the spring 402 into its thermal memory shape), or passively, including simply allowing a platform for the top section 510 and bottom section 520 to separate from each other, yet not detach.

The implant 500 may be configured to fit the spring 402 within the implant 500. For example, the top section 510 and bottom section 520 may each comprise suitable shapes 506 or undercuts 506 in which the spring 402 is housed. The top section 510 and/or bottom section 520 may comprise one or more sockets 508*a*,508*b*,which are configured to catch one or more of the first end 410, the second end 424, and/or the arch 416 of the spring 402 when the spring 402 expands, thereby locking the expanded spring 402 in place and securing the implant 500 in an expanded configuration (FIG. 7C and FIG. 7D). Expansion of the implant 500 as shown may, for example, allow for the implant 500 to fit within the site of implantation, and to engage, as appropriate, bone or tissue in the body to facilitate integration of the implant 500.

FIG. 8A and FIG. 8B show an example of an implant 500 in a compact and expanded state, which is mediated by the activation of a thermal memory spring 402. In the example shown, the implant 500 is configured to utilize the spring 402 shown in FIG. 2A and FIG. 2B, although the implant 500 may utilize any spring 402 described or exemplified herein.

The implant 500 may comprise an expandable box, with a plurality of sidewalls 512. Each sidewall 512 separates from an adjacent sidewall 512 as the implant 500 expands. The sidewalls 512 may comprise panels 511, 513, and may be connected to each other through at least one movable joint 504. The panels 511, 513 may be at right angles to each other. The implant 500 may comprise a front panel 522 and a rear panel 524. The movable joint 504 facilitates separation of sidewalls 512, and may do so actively, including moving each sidewall 512 away from an adjacent sidewall 512 (e.g., the movable joint 504 may be actuated by the expansion of the spring 402 into its thermal memory shape), or passively, including simply allowing a platform for the sidewalls 512 to separate from each other, yet not detach.

The implant 500 may be configured to fit the spring within the implant 500. For example, the implant 500 may comprise a center cavity 502, which may comprise compatible shapes 506 or undercuts 506 (not shown) in which the spring 402 is housed. The center cavity 502 may comprise one or more sockets 508 (not shown), which are configured to catch the first end 410, second end 414, and/or arch 416 of the spring 402 when the spring 402 expands, thereby locking the expanded spring 402 in place and securing the implant 500 in an expanded configuration (FIG. 8B). When the spring 402 is activated, and forms the arches 416a,416b,the arches 416a,416b push against the sidewalls 512, and force each sidewall 512 apart via the movable joints 504, as shown in FIG. 8B. In addition, the arches 416a,416b,and/or re-shaping of the spring 402 also may optionally force the front panel 522 and/or the rear panel 524 outward. Expansion of the implant 500 as shown may, for example, allow for the implant 500 to fit within the site of implantation, and to engage, as appropriate, bone or tissue in the body to facilitate integration of the implant 500.

An arch-forming spring 402 may be used with an implant 500 as shown in FIG. 9A through FIG. 9D. In the example shown, the implant 500 is configured to utilize the spring 402 shown in FIG. 2C and FIG. 2D, although the implant 500 may utilize any spring 402 described or exemplified herein.

The implant 500 preferably is comprised of two primary sections, a top section 510 and a bottom section 520. The top section 510 and bottom section 520 preferably are not directly connected to each other such that they may be separated when the implant 500 expands, as detailed below. The top section 510 and bottom section 520 may be indirectly connected to each other through at least one movable joint 504 that holds these sections 510, 520 together to form the implant 500. The movable joint 504 may comprise a hinge 504. When the implant 500 is not expanded, the at least one movable joint/hinge 504 is/are substantially closed such that the top section 510 and bottom section 520 may contact each other or at least be in close proximity to each other, as shown in FIGS. 9A and 9B. When the implant 500 expands, the at least one movable joint/hinge 504 opens such that the top section 510 and bottom section 520 separate, but do not become detached from the implant 500. The movable joint/hinge 504 is operably connected to each of the top section 510 and bottom section 520.

Figure 9D:
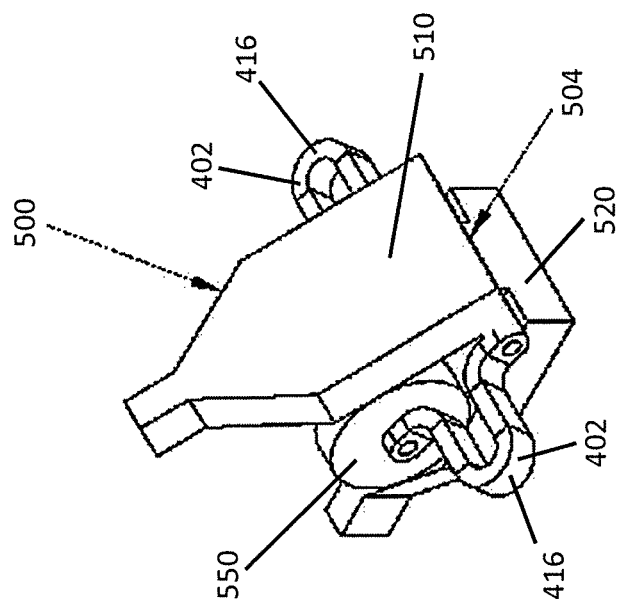
FIG. 9D shows a perspective view of the shape-memory spring and implant of FIG. 9A, with the spring in an activated state that advances the expansion roller toward a joint between the top and bottom sections of the implant.
Figure 9C:
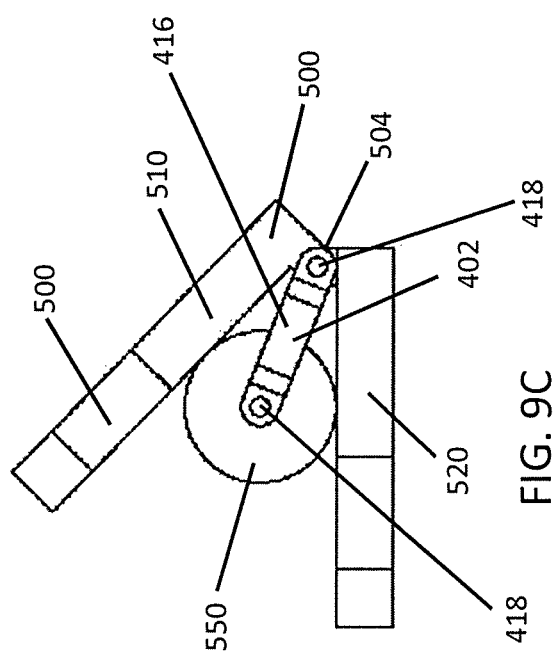
FIG. 9C shows a side perspective of the shape-memory spring and implant of FIG. 9A, with the spring in an activated state that advances the expansion roller toward a joint between the top and bottom sections of the implant.

The implant may comprise an expansion roller 550. The expansion roller 550 is operably connected to the spring 402, for example, by way of the spring connectors 418, and the roller 550 may be external to the main body of the implant 500. The spring 402 may also be operably connected to a surface of the main body of the implant 500, for example, by way of the spring connectors 418. The spring 402 may be connected to either the top section 510, the bottom section 520, or both sections 510, 520. Movement of the expansion roller 550 is effectuated by the activation of the thermal memory spring 402. For example, as the spring 402 assumes its thermal memory shape, its elongate profile contracts as the arch 416 forms, thereby pulling the expansion roller 550 toward the main body of the implant 500, eventually forcing the top section 510 and bottom section 520 apart along the hinge 504, as shown in FIG. 9C and FIG. 9D. In some aspects, the internal surfaces of the top section 510 and bottom section 520 may each comprise suitable undercuts 506 (not shown) or sockets 508 (not shown), which are configured to engage the expansion roller 550, thereby locking the expansion roller 530 in place and securing the implant 500 in an expanded configuration (FIG. 9C and FIG. 9D). Expansion of the implant 500 as shown may, for example, allow for the implant 500 to fit within the site of implantation, and to engage, as appropriate, bone or tissue in the body to facilitate integration of the implant 500.

Figure 10B:
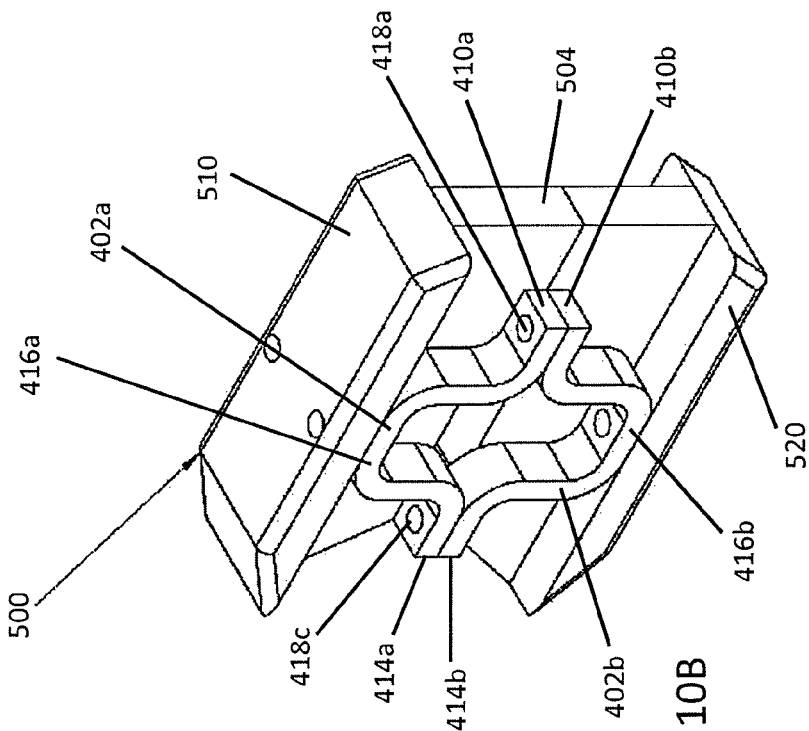
FIG. 10B shows the shape-memory springs and implant of FIG. 10A, with each of the springs in an activated state that expands the implant.
Figure 10A:
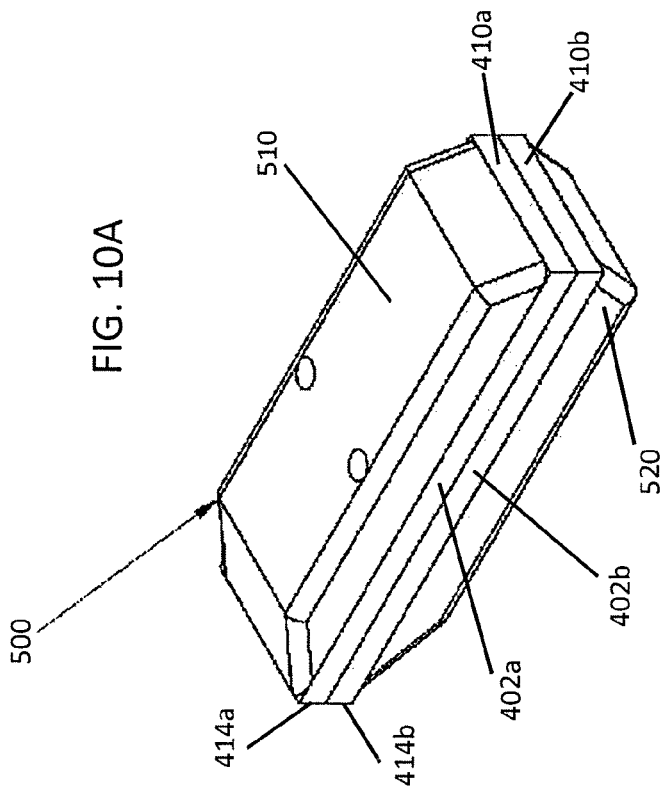
FIG. 10A shows an example of a non-expanded implant with two shape-memory springs in a relaxed state between the top and bottom sections of the implant.

FIG. 10A and FIG. 10B show an example of an implant 500 in a compact and expanded state, which is mediated by the activation of a thermal memory spring 402. In the example shown, the implant 500 is configured to utilize the spring 402 shown in FIG. 3A and FIG. 3B, although the implant 500 may utilize any spring 402 described or exemplified herein.

The implant 500 preferably is comprised of two primary sections, a top section 510 and a bottom section 520. The top section 510 and bottom section 520 preferably are not directly connected to each other such that they may be separated when the implant 500 expands, as detailed below. The top section 510 and bottom section 520 may be indirectly connected to each other through at least one movable joint 504 that bridges the top section 510 to the bottom section 520 to form the implant 500. When the implant 500 is not expanded, the at least one movable joint 504 is/are substantially closed such that the top section 510 and bottom section 520 may contact each other or at least be in close proximity to each other, as shown in FIG. 10A. When the implant 500 expands, the at least one movable joint 504 opens such that the top section 510 and bottom section 520 separate, but do not become detached from the implant 500. The movable joint 504 is operably connected to each of the top section 510 and bottom section 520. The movable joint 504 facilitates separation of the top section 510 and the bottom section 520, and may do so actively, including moving either or both of the top section 510 and the bottom section 520 (e.g., the movable joint 504 may be actuated by the expansion of the spring 402 into its thermal memory shape), or passively, including simply allowing a platform for the top section 510 and bottom section 520 to separate from each other, yet not detach.

The thermal memory spring 402 is placed between the top section 510 and the bottom section 520. In some aspects, two thermal memory springs 402a,402b are placed between the top section 510 and the bottom section 520. Each spring 402a,402b may be placed in an opposing orientation such that when the springs 402a,402b expand, they expand in opposite directions (FIGS. 10B). In some aspects, one thermal memory spring 402 is placed between the top section 510 and the bottom section 520, but when the spring 402 expands, each arch 416 (on either side of the slot 415) expands in an opposite direction relative to the other arch 416. The movable joint 504 may be positioned within the slot 415 of the springs 402a,402b,such that arches 416 straddle the movable joint 504.

When the spring 402 is activated, and forms the arches 416a,416b (FIG. 10B), the arches 416 push against the underside of the top section 510 and bottom section 520, and force the top section 510 and bottom section 510 apart about the movable joint 504, as shown in FIG. 10B. Expansion of the implant 500 as shown may, for example, allow for the implant 500 to fit within the site of implantation, and to engage, as appropriate, bone or tissue in the body to facilitate integration of the implant 500.

Figures 11A, 11B:
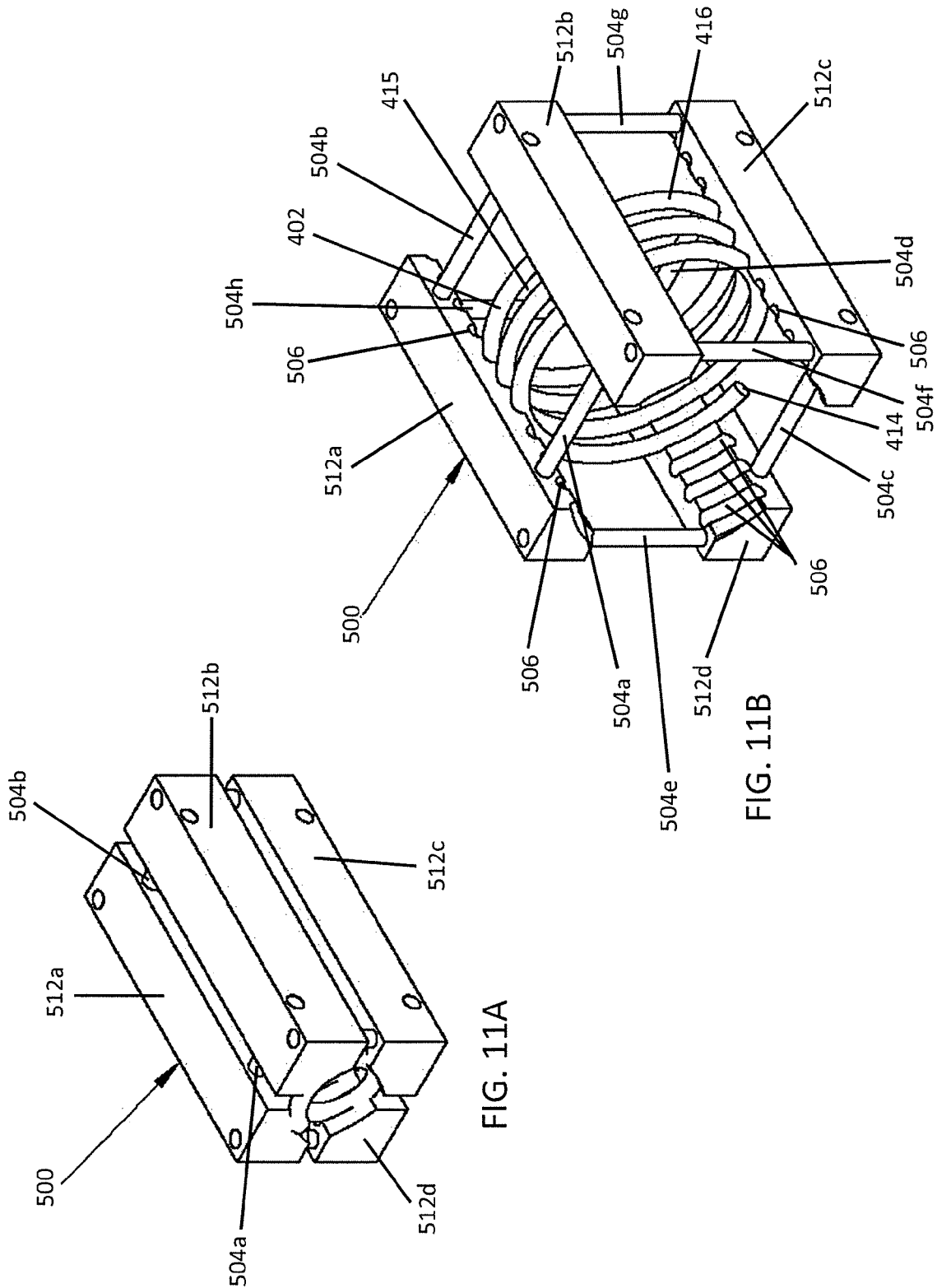
FIG. 11A shows an example of a non-expanded implant containing a solenoid-shaped shape-memory spring in a relaxed state.
FIG. 11B shows the shape-memory spring and implant of FIG. 11A, with the spring in an activated state that expands the implant.

FIG. 11A and FIG. 11B show an example of an implant 500 in a compact and expanded state, which is mediated by the activation of a thermal memory spring 402. In the example shown, the implant 500 is configured to utilize the spring 402 shown in FIG. 4A and FIG. 4B, although the implant 500 may utilize any spring 402 described or exemplified herein.

The implant 500 may comprise an expandable box or cage, with a plurality of sidewalls 512a-d connected to each other through at least one movable joint 504a-d that holds these sidewalls 512a-d together. The internal surfaces of each sidewall 512a-d may comprise a plurality of slots 506 or grooves 506. The plurality of arches 416 and slots 415 of the spring 402 fit within these grooves 506, thereby securing the spring 402 in place within the interior of the implant 500. The movable joint 504a-d facilitates separation of the sidewalls 512a-d from adjacent sidewalls 512a-d, and may do so actively, including moving the sidewalls 512a-d apart (e.g., the movable joint 504 may be actuated by the expansion of the spring 402 into its thermal memory shape), or passively, including simply allowing a platform for each sidewall 512 to separate from an adjacent sidewall 512, yet not detach.

When the spring 402 is activated, and the arches 416 expand outward, enhancing the diameter of the coil (FIG. 11B), the arches 416 push against the sidewalls 512, and force each sidewall 512a-d apart along each movable joint 504a-d,as shown in FIG. 11B. Expansion of the implant 500 as shown may, for example, allow for the implant 500 to fit within the site of implantation, and to engage, as appropriate, bone or tissue in the body to facilitate integration of the implant 500.

FIGS. 12A-12C show an example of an implant 500 in a compact and expanded state, which is mediated by the activation of a thermal memory spring 402. In the example shown, the implant 500 is configured to utilize the spring 402 shown in FIG. 5A and FIG. 5B, although the implant 500 may utilize any spring 402 described or exemplified herein.

The implant 500 preferably is comprised of three primary sections, a top section 510, a bottom section 520, and a central section 530 between the top section 510 and the bottom section 520 (FIG. 12C). The top section 510, bottom section 520, and central section 530 preferably are not directly connected to each other such that they may be separated when the implant 500 expands, as detailed below. The top section 510, bottom section 520, and central section 530 may be indirectly connected to each other through at least one movable joint 504 that bridges these sections 510, 520, 530 together to form the implant 500. When the implant 500 is not expanded, the at least one movable joint 504 is/are substantially closed such that the central section 530 is in contact with or at least in proximity to the top section 510 and bottom section 520 as shown in FIG. 12A. When the implant 500 expands, the at least one movable joint 504 opens such that the top section 510 and bottom section 520 separate from the central section 530, but do not become detached from the implant 500. The movable joint 504 is operably connected to each of the top section 510 and bottom section 520, and in some aspects, to the central section 530. The movable joint 504 facilitates separation of the top section 510 and the bottom section 520, and may do so actively, including moving either or both of the top section 510 and the bottom section 520 (e.g., the movable joint 504 may be actuated by the expansion of the spring 402 into its thermal memory shape), or passively, including simply allowing a platform for the top section 510 and bottom section 520 to separate away from each other and the central section 530, yet not detach.

The top section 510, bottom section 520, and central section 530 may each comprise undercuts 506 into which the thermal memory spring 402 is placed within the implant 500, and optionally may comprise an aperture 540 that allows one or more of the ends 410, 414 of the spring to extend out of the implant 500 (FIG. 12A and FIG. 12B). The implant 500 may comprise one or more connectors 518a, 518b that connect with the spring connectors 418 to affix the spring 402 to the implant 500 and secure the spring 402 in place within the aperture 540. The implant connectors 518a,518b are preferably present on the central section 530. When the spring 402 is activated, the truss arms 421a,421b extend outward, pushing against the internal walls of each of the spring arms 411a,411b until the truss arms 421a,421b engage and lock within the notch 425. The expansion of the spring arms 411a,411b engage sockets 508 or undercuts 506 in the inner walls of the top section 510 and bottom section 520, and thereby force the top section 510 and bottom section 520 apart and away from the central section 530 (FIG. 12B and FIG. 12C). The first end 410 and second end 414 of the spring 402 may extend beyond the outer plane of the top section 510 and bottom section 520 as shown in FIG. 12C, but need not extend beyond this outer plane (e.g., through the aperture 540, if an aperture 540 is present). If the first end 410 and second end 414 do extend beyond the outer plane, they may help to engage bone or tissue at the site of implantation, thereby helping to secure the implant 500 in place. Expansion of the implant 500 as shown may, for example, allow for the implant 500 to fit within the site of implantation, and to engage, as appropriate, bone or tissue in the body to facilitate integration of the implant 500.

Extension of the first end 410 and second end 414 of the spring 402 outside of the implant 500 may provide for an anti-migration or anti expulsion benefit for the implant 500. For example, when protruding out from the top section 510 and/or bottom section 520, the first end 410 and second end 414 may function as an anchor for the implant 500 as each of the first end 410 and second end 414 will contact bone surfaces, and embed into the bone. Engaging the bone will substantially reduce or eliminate the risk of the implant 500 becoming dislodged or otherwise moving into a different position or location. The engagement of the and first end 410 and second end 414 with the bone surface may, in some aspects, form a connection with the bone akin to a screw-in connection with the bone. Thus, the protruding first end 410 and second end 414, in contacting opposing bone surfaces, may aid the healing process, including the reduction of localized stress-induced necrosis.

FIG. 13A and FIG. 13B show an example of an implant 500 in a compact and expanded state, which is mediated by the activation of a thermal memory spring 402. In the example shown, the implant 500 is configured to utilize the spring 402 shown in FIG. 6A and FIG. 6B, although the implant 500 may utilize any spring 402 described or exemplified herein.

The implant 500 may comprise an expandable box, with a plurality of sidewalls 512a-d. The sidewalls 512 may comprise panels 511, 513, and may be connected to each other through at least one movable joint 504. The panels 511, 513 may be at right angles to each other. The movable joint 504 facilitates separation of sidewalls 512, and may do so actively, including moving each sidewall 512 away from an adjacent sidewall 512 (e.g., the movable joint 504 may be actuated by the expansion of the spring 402 into its thermal memory shape), or passively, including simply allowing a platform for the sidewalls 512 to separate from each other, yet not detach.

The implant 500 may configured to fit the spring 402 within the implant 500. For example, the implant 500 may comprise a center cavity 502, which may comprise compatible shapes 506 or undercuts 506 in which the spring 402 is housed. The center cavity 502 may comprise one or more sockets 508, which are configured to catch the first end 410a, b and second end 424a, b, and/or arch 416a, b of the spring 402 when the spring 402 expands, thereby locking the expanded spring 402 in place and securing the implant 500 in an expanded configuration (FIG. 13B). When the spring 402 is activated, the truss arms 421a, 421b, 421c, and 42d extend outward until the truss arms 421a, 421b, 421c, and 42d engage and lock within the notch 425a-d on the internal walls of each of the spring arms 411a, 411b, 411c, and 411d. The expansion of the spring arms 411a, 411b, 411c, and 411d may allow the ends 410a, 410b, 414a, and 414b to engage sockets 508 or undercuts 506 in the inner cavity 502 (underside of each sidewall 112a-d or sub-panel 511, 513 thereof), and force each sidewall 512 apart from adjacent sidewalls 512, as shown in FIG. 13B and FIG. 13C. Expansion of the implant 500 as shown may, for example, allow for the implant 500 to fit within the site of implantation, and to engage, as appropriate, bone or tissue in the body to facilitate integration of the implant 500.

FIG. 14A and FIG. 14B show another embodiment of the shape-memory spring 402, which comprises a metal with a thermal shape memory. The spring 402 comprises a first end 410, a second end 414, and a mid-section 412 between the first end 410 and second end 414. The spring 402 comprises a first spring arm 411a and a second spring arm 411b, and also comprises at least one arch 416 within the mid-section 412, and the arch 416 may be substantially in the center of the spring 402 as shown in FIG. 14A or may be off-center, or may be more proximal to the first end 410 and/or the second end 414. In this embodiment, the arch 416 is present in the spring 402 in the relaxed state. When the spring 402 is activated, the arch 416 opens such that at least one of the first spring arm 411a and the second spring arm 411b separate further from each other, for example, as shown in FIG. 14B.

On the internal surface of at least the first spring arm 411a or the second spring arm 411b, the spring 402 comprises at least one truss arm 421, for example, as shown in FIG. 14B. When the spring 402 is in its relaxed state, the truss arm 421 may lie substantially flat against the internal surface of the first arm 411a or the second arm 411b, or may be seated/inset within a socket 423 in the first arm 411a or the second arm 411b. The truss arm 421 may also comprise a portion of the first arm 411a or the second arm 411b that is a cut-out of the first arm 411a or the second arm 411b, thereby allowing the truss arm 421 to move independently of the main body of the first arm 411a or second arm 411b. When the spring 402 is activated, the truss arm 421 extends outward along the internal surface of the opposite spring arm 411a or 411b from which the truss arm 421 is connected, and extends until the truss arm end 420 enters into the notch 425, which is on the internal surface of the opposite spring arm 411a or 411b from which the truss arm 421 is connected (FIG. 14B), and in doing so, the truss arm 421 becomes locked in place. The engagement of the truss arm end 420 with the notch 425 locks the activated spring 402 into an expanded state.

Figure 15B:
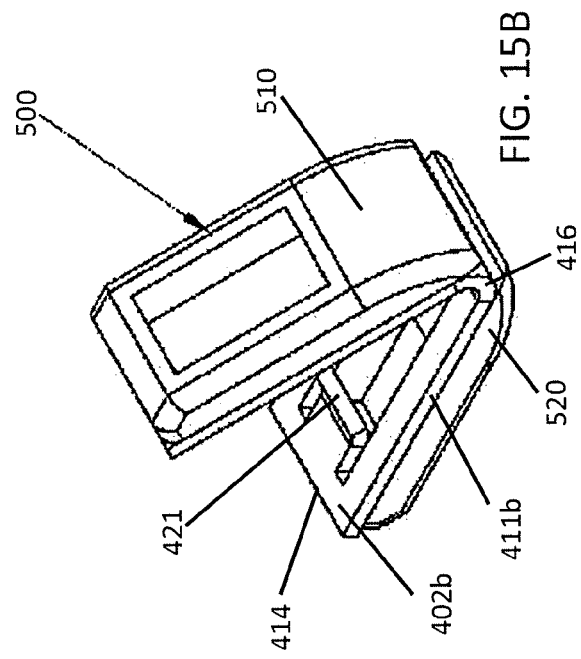
FIG. 15B shows a perspective view of the implant of FIG. 15A in which the spring is in an activated state that expands the implant.
Figure 15D:
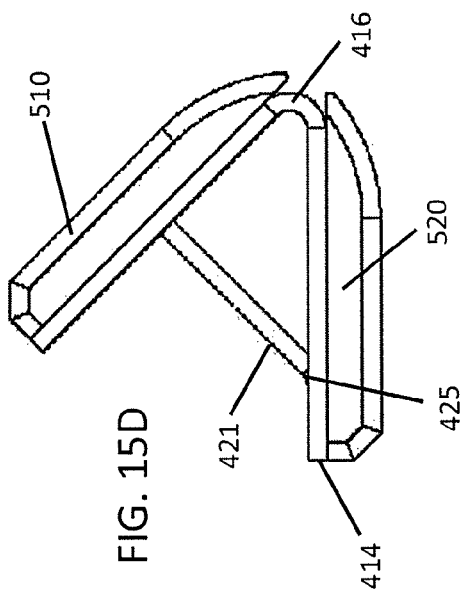
FIG. 15D shows a side perspective of the expanded implant shown in FIG. 15B.
Figure 15A:
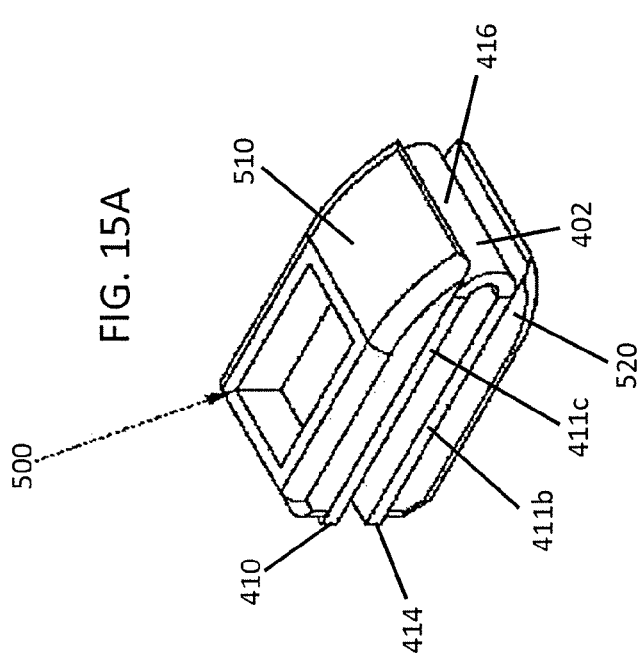
FIG. 15A shows an example of a non-expanded implant in which an arched shape-memory spring in a relaxed state.
Figure 15C:
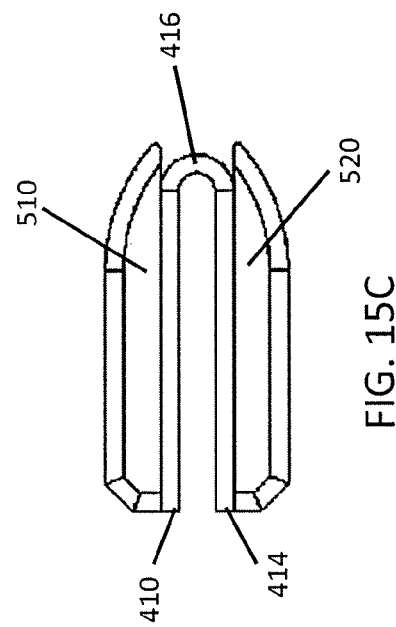
FIG. 15C shows a side perspective of the non-expanded implant shown in FIG. 15A.
Figure 16B:
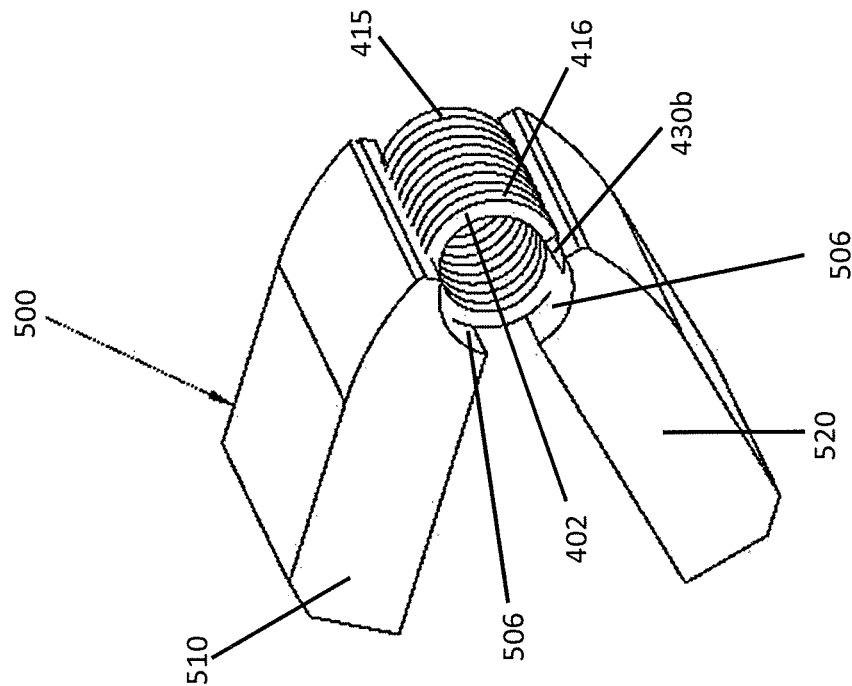
FIG. 16A shows an example of a non-expanded implant with a solenoid-shaped shape-memory spring and expansion arms in a relaxed state; and, FIG. 16B shows a perspective view of the implant shown in FIG. 16A in an activated state that expands the implant.
Figure 16A:
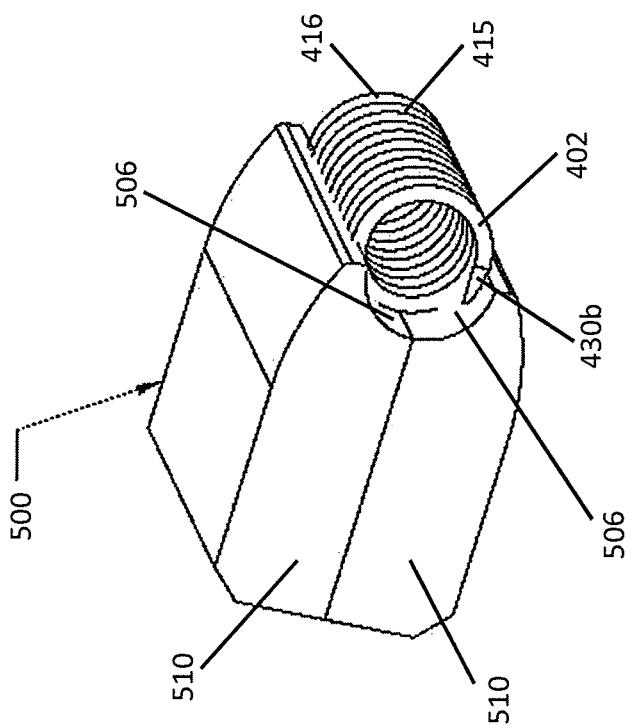

FIGS. 15A-15C show an example of an implant 500 in a compact and expanded state, which is mediated by the activation of a thermal memory spring 402. In the example shown, the implant 500 is configured to utilize the spring 402 shown in FIG. 14A and FIG. 14B, although the implant 500 may utilize any spring 402 described or exemplified herein. FIGS. 16A and 16B show an example of an implant 500 in a compact and expanded state, which is mediated by the activation of a thermal memory spring 402. In the example shown, the implant 500 is configured to utilize the spring 402 shown in FIG. 4C and FIG. 4D, although the implant 500 may utilize any spring 402 described or exemplified herein.

The implant 500 preferably is comprised of two primary sections, a top section 510 and a bottom section 520. The top section 510 and bottom section 520 preferably are not directly connected to each other such that they may be separated when the implant 500 expands, as detailed below. The top section 510 and bottom section 520 may be indirectly connected to each other through at least one movable joint 504 that holds these sections 510, 520 together to form the implant 500 (not shown). The top section 510 and bottom section 520 may not be connected to each other at all, even indirectly, such that each of the top section 510 and bottom section 520 attach directly to one of the spring arms 411a or 411b of the spring 402, with the spring 402 serving as an intermediary to form the full implant 500 (FIG. 15A-15D). The top section 510 and bottom section 520 may not be connected to each other at all such that each of the top section 510 and bottom section 520 attach directly to one or more of the extension arms 430a or 430b of the spring 402, with the spring 402 serving as an intermediary to form the full implant 500 (FIG. 16A and 16B). When the implant 500 is not expanded, the top section 510 and bottom section 520 may be in close proximity to each other, as shown in FIG. 15A and FIG. 16A.

The thermal memory spring 402 is placed between the top section 510 and the bottom section 520. As shown in the FIG. 15B, when the spring 402 expands, at least one of the first arm 411a or second arm 411b expands outward from the opposite arm 411a or 411b. As the arm 411a or 411b expands, the top section 510 or bottom section 520 which is attached to the expanding arm 411a or 411b moves upward and away from the opposite section 510 or 520 (FIG. 15B and FIG. 15D). As shown in the FIG. 16B, when the spring 402 expands, at least one of the extension arms 430a, 430b expands in a direction away from its relaxed position. As the extension arm 430a, 430b expands, the top section 510 or bottom section 520 which is attached to the extension arm 430a and/or 430b moves upward and away from the opposite section 510 or 520 (FIG. 16B). Separation of the top section 510 from the bottom section 520 may be at a substantially uniform distance along the internal surfaces of the top section 510 and bottom section 520, or may be uneven, with one end expanding at a greater distance than the other end, as shown in FIG. 15D and FIG. 16B. Expansion of the implant 500 as shown in the figures may, for example, allow for the implant 500 to fit within the site of implantation, and to engage, as appropriate, bone or tissue in the body to facilitate integration of the implant 500.

Methods of using the thermal memory springs 402 and expandable implants 500 described herein include implanting an expandable implant 500 into a patient in need thereof. Preferably, the implant 500 is inserted into the patient in its compact, non-expanded form. For example, the implant 500 includes the thermal memory spring 402 in its non-activated, non-thermal memory shape or state such that the spring 402 is not expanding the implant 500, and the implant 500 can be maneuvered through dissected tissue and into the location where it will reside within the body. The implant 500, is therefore preferably implanted while at a temperature that is below the temperature that instigates the transition and/or activation of the spring 402 into its thermal memory shape or state, for example, a temperature below that of human body temperature or below 37 degrees C. The patient preferably is a human being.

The methods may optionally include warming or heating the implant 500 to human body temperature, or to the temperature at which the thermal memory spring 402 transitions and/or activates into its thermal memory shape or state. The implant 500 may be so warmed or heated after the implant 500 has been implanted into and positioned as desired into the location where it will reside in the body so as to facilitate expansion of the implant 500. The implant 500 may be warmed or heated according to any suitable methodology. In some aspects, the methods may include warming or heating (e.g., pre-heating) the implant 500 to a temperature that is below, yet near to human body temperature or the temperature at which the thermal memory spring 402 transitions into its thermal memory shape or state, so as to facilitate further warming or heating at the implantation site, the latter of which brings the implant 500 to the thermal memory activation temperature.

The methods may optionally include the steps of incising and dissecting tissue in the body, and may include the step of inserting the implant 500 into and through the incision and dissection pathway, and may include the step of inserting the implant 500 into the location of implantation, or where the implant 500 will reside within the body. The methods may optionally include the step of positioning the implant 500 within the location of implantation. Preferably, insertion and positioning of the implant 500 within the body are carried out before the implant 500 is expanded by warming to the thermal memory transition temperature of the spring 402 that is part of the implant 500. The methods may optionally include the step of positioning the implant 500 within the location of implantation after the implant 500 has expanded.

In some aspects, the methods may further include the step of inserting a bone graft material into the implant 500 or subsections thereof, or onto any surface of the implant 500 that will contact bone within the body, or onto any other surface of the implant 500 where it is desired that the implant 500 integrate with new bone or otherwise facilitate new bone growth. Inclusion of a bone graft material may serve to facilitate osteointegration of the implant 500, to reinforce of the implant 500, and to improve bone graft containment. The bone graft material may comprise cancellous autograft bone, allograft bone, demineralized bone matrix (DBM), porous synthetic bone graft substitute, bone morphogenic protein (BMP), or any combination thereof.

The foregoing methods are advantageous as the incision and insertion pathways are minimized relative to traditional procedures in which non-expandable, standard implants are used. The latter procedures require larger incisions and larger tissue dissection as part of the insertion pathway in order to accommodate the larger size of the non-compact, non-expandable implants.

Kits may include any implant 500 described or exemplified herein, and instructions for using the implant 500 in any method described or exemplified herein. The kits may further include surgical or implantation tools, including but not limited to scalpels, distractors, rasps, implant manipulation tools, and other tools that would be used in the implantation of an implant 500 within the body.

The invention is not limited to the embodiments described and exemplified above, but is capable of variation and modification within the scope of the appended claims.

What is claimed:

1. An expandable interbody device, comprising an interbody implant comprising one or more moveable joints, and a top portion and a bottom portion that comprise undercuts housing a thermal memory spring within the interbody implant, and one or more sockets into which one or more ends or arches of the thermal memory spring embed when the thermal memory spring expands into a pre-established thermal memory shape, thereby locking the implant in an expanded state, and that are independently operably connected to one of the one or more moveable joints such that movement of the one or more moveable joints moves the top portion and the bottom portion away from each other, wherein the thermal memory spring comprises a thermal memory material that is activated to expand the spring into the pre-established thermal memory shape at a temperature at or above about 37 degrees C., and wherein expansion of the spring into the pre-established thermal memory shape moves the one or more moveable joints of the implant.

2. The expandable interbody device of claim 1, wherein the thermal memory material comprises nitinol or alloy thereof.

3. The expandable interbody device of claim 1, wherein the pre-established thermal memory shape includes at least one arch substantially in the middle of the thermal memory spring.

4. The expandable interbody device of claim 1, wherein the thermal memory spring comprises at least one spring arm, and at least one truss arm that, extends outward until an end of the at least one truss arm embeds in a notch on an internal surface of the at least one spring arm when the thermal memory spring expands into the pre-established thermal memory shape, thereby locking the at least one spring arm in a pre-established thermal memory position.

5. The expandable interbody device of claim 1, wherein expansion of the thermal memory spring into the pre-established thermal memory shape positions the one or more ends of the spring outside of the top portion, the bottom portion, or both the top portion and bottom portion of the implant for engaging one or more bone surfaces.

6. The expandable interbody device of claim 1, wherein the implant further comprises a central section.

7. An expandable interbody device, comprising an interbody implant comprising one or more moveable joints, and a plurality of sidewalls that comprise undercuts housing a thermal memory spring within the interbody implant, and one or more sockets into which one or more ends or arches of the thermal memory spring embed when the thermal memory spring expands into a pre-established thermal memory shape, thereby locking the implant in an expanded state, and that are independently operably connected to one of the one or more moveable joints such that movement of the one or more moveable joints moves at least one sidewall away from an adjacent sidewall, wherein the thermal memory spring comprises a thermal memory material that is activated to expand the spring into the pre-established thermal memory shape at a temperature at or above about 37 degrees C., and wherein expansion of the spring into the pre-established thermal memory shape moves the one or more moveable joints of the implant.

8. The expandable interbody device of claim 7, wherein the thermal memory material comprises nitinol or alloy thereof.

9. The expandable interbody device of claim 7, wherein the thermal memory spring comprises at least one spring arm, and at least one truss arm that extends outward until an end of the at least one truss arm embeds in a notch on an internal surface of the at least one spring arm when the thermal memory spring expands into the pre-established thermal memory shape, thereby locking the at least one spring arm in a pre-established thermal memory position.

10. The expandable interbody device of claim 7, wherein the thermal memory spring comprises a plurality of spring arms, and a plurality of truss arms that extend outward until an end of each truss arm embeds in a notch on an internal surface of an adjacent spring arm when the thermal memory spring expand into the pre-established thermal memory shape, thereby locking each spring arm in a pre-established thermal memory position.

11. An expandable interbody device, comprising an interbody implant comprising a top portion and a bottom portion that comprise undercuts housing a thermal memory spring within the interbody implant, the thermal memory spring comprising a thermal memory material that is activated to expand the spring into a pre-established thermal memory shape at a temperature at or above about 37 degrees C., and at least one spring arm, and at least one truss arm that-extends outward until an end of the at least one truss arm embeds in a notch on an internal surface of the at least one spring arm when the thermal memory spring expands into the pre-established thermal memory shape, thereby locking the at least one spring arm in a pre-established thermal memory position, wherein expansion of the spring into the pre-established thermal memory shape moves at least a section of the top portion away from at least a section of the bottom portion to expand the implant.

12. The expandable interbody device of claim 11, wherein the thermal memory material comprises nitinol or alloy thereof.

* * * * *